US012583865B2

(12) United States Patent
McChesney et al.

(10) Patent No.: US 12,583,865 B2
(45) Date of Patent: *Mar. 24, 2026

(54) BIOLOGICALLY ACTIVE TAXANE ANALOGS AND METHODS OF TREATMENT BY ORAL ADMINISTRATION

(71) Applicant: Tapestry Pharmaceuticals, Inc., Atlanta, GA (US)

(72) Inventors: James D. McChesney, Etta, MS (US); Gilles H. Tapolsky, Louisville, KY (US); David Lloyd Emerson, Longmont, CO (US); John Marshall, Washington, DC (US); Michael Kurman, Upper Saddle River, NJ (US); Manuel R. Modiano, Tucson, AZ (US)

(73) Assignee: Tapestry Pharmaceuticals, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/476,003

(22) Filed: Sep. 27, 2023

(65) Prior Publication Data

US 2024/0294540 A1 Sep. 5, 2024

Related U.S. Application Data

(63) Continuation of application No. 17/539,578, filed on Dec. 1, 2021, now Pat. No. 11,873,308, which is a (Continued)

(51) Int. Cl.
*A61K 31/357* (2006.01)
*A61K 31/495* (2006.01)
(Continued)

(52) U.S. Cl.
CPC .......... *C07D 493/06* (2013.01); *A61K 31/357* (2013.01); *A61K 31/495* (2013.01); *A61K 39/3955* (2013.01); *A61K 45/06* (2013.01)

(58) Field of Classification Search
CPC ..................................................... C07D 493/06
See application file for complete search history.

(56) References Cited

U.S. PATENT DOCUMENTS

| | | | |
|---|---|---|---|
| 5,352,806 A | 10/1994 | Gunawardana et al. | |
| 5,635,531 A | 6/1997 | Chen | |

(Continued)

FOREIGN PATENT DOCUMENTS

| | | |
|---|---|---|
| EP | 0856512 A2 | 8/1998 |
| EP | 1148055 A1 | 10/2001 |

(Continued)

OTHER PUBLICATIONS

Ali et al., "Novel Cytotoxic 3'-(tert-Butyl) 3'-Dephenyl Analogs of Paclitaxel and Docetaxel", J. Med. Chem., vol. 38, pp. 3821-3828 (1995).

(Continued)

*Primary Examiner* — Benjamin J Packard
(74) *Attorney, Agent, or Firm* — Morgan, Lewis & Bockius LLP

(57) ABSTRACT

The present invention relates to a novel chemical compound for use in the treatment of cancer, to compositions containing said compound, methods of manufacture and combinations with other therapeutic agents.

(Continued)

S-(1)

18 Claims, 16 Drawing Sheets

Related U.S. Application Data continuation of application No. 16/929,719, filed on Jul. 15, 2020, now Pat. No. 11,220,512, which is a continuation of application No. 16/569,302, filed on Sep. 12, 2019, now Pat. No. 10,745,408, which is a continuation of application No. 15/797,145, filed on Oct. 30, 2017, now Pat. No. 10,450,323, which is a continuation of application No. 13/950,316, filed on Jul. 25, 2013, now Pat. No. 9,802,951, which is a continuation of application No. 13/620,852, filed on Sep. 15, 2012, now Pat. No. 8,552,056, which is a continuation of application No. 12/873,477, filed as application No. PCT/US2008/055384 on Feb. 28, 2008, now Pat. No. 8,273,789.

(60) Provisional application No. 60/911,607, filed on Apr. 13, 2007, provisional application No. 60/908,459, filed on Mar. 28, 2007.

(51) Int. Cl.
| | | |
|---|---|---|
| *A61K 39/395* | (2006.01) | |
| *A61K 45/06* | (2006.01) | |
| *C07D 493/06* | (2006.01) | |

(56) References Cited

U.S. PATENT DOCUMENTS

| | | | |
|---|---|---|---|
| 7,745,650 | B2 | 6/2010 | Zygmunt et al. |
| 7,879,904 | B2 | 2/2011 | Zygmunt et al. |
| 2005/0148657 | A1 | 7/2005 | Zygmunt et al. |
| 2009/0156828 | A1 | 6/2009 | Henri et al. |
| 2010/0324128 | A1 | 12/2010 | Zygmunt et al. |
| 2011/0135712 | A1 | 6/2011 | McChesney et al. |

FOREIGN PATENT DOCUMENTS

| | | | | |
|---|---|---|---|---|
| EP | 1228759 | A1 | 8/2002 | |
| EP | 1285920 | A2 | 2/2003 | |
| EP | 1785416 | A2 | 5/2007 | |
| EP | 1973892 | A1 | 6/2007 | |
| EP | 1810968 | A2 | 7/2007 | |
| EP | 1664033 | B1 | 11/2007 | |
| EP | 2007739 | A2 | 11/2007 | |
| EP | 1894921 | A2 | 3/2008 | |
| FR | 270793 | A1 | 1/1995 | |
| FR | 2715846 | A1 | 8/1995 | |
| WO | 9209589 | A1 | 11/1991 | |
| WO | 9321173 | A1 | 10/1993 | |
| WO | 9408984 | A1 | 4/1994 | |
| WO | 9410996 | A1 | 5/1994 | |
| WO | 9420485 | A1 | 9/1994 | |
| WO | 9501969 | A1 | 1/1995 | |
| WO | 9629321 | A1 | 9/1996 | |
| WO | 0156564 | A1 | 8/2001 | |
| WO | 0157027 | A1 | 8/2001 | |
| WO | 03053350 | A2 | 7/2003 | |
| WO | 2005030150 | A2 | 4/2005 | |
| WO | 2006124737 | A2 | 11/2006 | |
| WO | 2007073383 | A1 | 6/2007 | |
| WO | 2007075870 | A2 | 7/2007 | |
| WO | 2008121476 | A1 | 10/2007 | |
| WO | 2007126893 | A2 | 11/2007 | |
| WO | 2008109360 | A1 | 9/2008 | |
| WO | WO-2008106621 | A1 * | 9/2008 | .............. A61P 35/00 |

OTHER PUBLICATIONS

Appendino et al., "The Chemistry and Occurrence of Taxane Derivatives.XIII (*). The Oxidation of 10-Deacetylbaccatin III (**)", Gazzetta Chimica Italiana, vol. 124, pp. 253-257 (1994).

Appendino et al., "The Reductive Fragmentation of 7-Hydroxy-9, 10-dioxotaxoids", Eur. J. Org. Chem, pp. 4422-4431 (2003).

Baldelli et al., "New Taxane Derivatives: Synthesis of Baccatin[14, 1-d]furan-2-one Nucleus and Its Condensation with the Norstatine Side Chain", J. Org. Chem., vol. 69, pp. 6610-6616 (2004).

Bunnage et al., "Asymmetric synthesis of anti-(2S,3S)- and syn-(2R,3S)- diaminobutanoic acid", Org. Biomol. Chem. vol. 1, pp. 3708-3715 (2003).

Datta et al., "Syntheses of Novel C-9 and C-10 Modified Bioactive Taxanes", Tetrahedron Letters, vol. 36, No. 12, pp. 1985-1988 (1995).

DeMattei et al., "An Efficient Synthesis of the Taxane-Derived Anticancer Agent ABT-271", J_ORg. Chem, vol. 66, pp. 3330-3337 (2001).

Didier et al., "2-Monosubstituted-1,3-Oxazolidines as Improved Protective Groups of N-Boc-Phenylisoserine in Docetaxel Preparation", Tetrahedron Letters, vol. 35, No. 15, pp. 2349-2352 (1994).

Georg et al., "Synthesis of Biologically Active Taxol Analogues with Modified Phenylisoserine Side Chains", J. Med.: Chem., vol. 35, pp. 4230-4237 (1992).

Georg et al., "The Chemistry of the Taxane Diterpene: Stereoselective Reductions of Taxanes", J. Org. Chem., vol. 53, pp. 8926-8934 (1998).

Hofer et al., Chemotherapy for malignant brain tumors of astrocytic and oligodendroglial lineage, J. Cancer Res Clir Oncol, vol. 127, pp. 91-95 (2001).

Johansen et al., "Phase I Evaluation of Oral and Intravenous Vinorelbine in Pediatric Cancer Patients: A Report frorr he Children's Oncology Group", Clin Cancer Res, vol. 12, No. 2, pp. 516-522 (2006).

Kingston et al., "Synthesis and Biological Evaluation of 1-Deoxypaclitaxel Analogues", J. Org. Chem., vol. 64, pp. 1814-1822 (1999).

Klein et al., "Antitumor Activity of 9(R)-Dihydrotaxane Analogs", J. Med. Chem., vol. 38, pp. 1482-1492 (1995).

Klein, "Synthesis of 9-Dihydrotaxol: A Novel Bioactive Taxane", Tetrahedron Letters, vol. 34, No. 13, pp. 2047-2050 (1993).

Kobayashi et al., "Effects of Taxoids from Taxus Cuspidata on Microtubule Depolymerization and Vincristine Accumulation in MDF Cells", Bioorganic & Medicinal Chemistry Letters, vol. 7, No. 4, pp. 393-398 (1997).

Lange et al., "An Approach to the A/B Substructure of 11(15-1)-Abeotaxanes. A Formal Synthesis of Compressanolide." Tetrahedron Letters, vol. 39, pp. 3639-3642 (1998).

Omuro et al., "Vinorelbine combined with a protracted course of temozolomide for recurrent brain Metastases: a phase I trial", Journal of Neuro-Oncology, vol. 78, pp. 277-280 (2006).

Samaranayake et al., "Modified Taxols. Reaction of Taxol with Electrophilic Reagents and Preparation of a Rearranged Taxol Derivative with Tubulin Assembly Activity", J. Org. Chem., vol. 56, pp. 5114-5119 (1991).

(56) References Cited

OTHER PUBLICATIONS

Office Action dated Mar. 14, 2007 for U.S. Appl. No. 10/951,555.
Office Action dated Sep. 14, 2007 for U.S. Appl. No. 11/834,489.
Office Action dated Dec. 26, 2007 for U.S. Appl. No. 11/834,489.
Office Action dated Dec. 24, 2008 for U.S. Appl. No. 11/680,563.
Office Action dated Dec. 31, 2008 for U.S. Appl. No. 11/743,849.
Office Action dated Mar. 27, 2009 for U.S. Appl. No. 10/951,555.
Office Action dated May 1, 2009 for U.S. Appl. No. 12/215,563.
Office Action dated Aug. 27, 2009 for U.S. Appl. No. 10/951,555.
Office Action dated Sep. 29, 2009 for U.S. Appl. No. 11/691,024.
Office Action dated Apr. 14, 2010 for U.S. Appl. No. 11/691,024.
Office Action for Japanese Application No. 2006-528316 dated Sep. 27, 2010.
English-language abstract for FR 2707293 , Jan. 13, 1995.
English-language abstract for FR 2715846, Aug. 11, 1995.
Office Action dated Aug. 24, 2018 for U.S. Appl. No. 15/797,145.
Office Action dated Mar. 13, 2018 for U.S. Appl. No. 15/797,145.
Zamir et al. Tetra. Lei. vol. 37 No. 36, pp. 6435-6438 (1996).

* cited by examiner

| DAY | 1 | 6 | 9 | 11 | 14 | 17 | 22 | 25 |
|---|---|---|---|---|---|---|---|---|
| % TUMOR VOLUME | | | | | | | | |
| CONTROL VEHICLE 200ul (Q2Dx4) | 100.00 | 228.02 | 291.96 | 300.79 | 302.77 | 334.12 | 385.13 | 380.94 |
| S-(1) (SK608-20.1) 10mg/kg (Q2Dx4) | 100.00 | 138.11 | 192.93 | 187.86 | 186.09 | 218.47 | 268.58 | 246.55 |
| S-(1) (SK608-20.1) 12mg/kg (Q2Dx4) | 100.00 | 145.94 | 186.27 | 168.78 | 147.42 | 198.71 | 185.37 | 221.82 |
| S-(1) (SK608-20.1) 14mg/kg (Q2Dx4) | 100.00 | 180.53 | 181.78 | 137.42 | 115.52 | 149.34 | 267.09 | 207.88 |
| | | | | | | | | |
| % BODY WEIGHT | 1 | 6 | 9 | 11 | 14 | 17 | 22 | 25 |
| CONTROL VEHICLE 200ul (Q2Dx4) | 100.00 | 101.69 | 101.42 | 101.57 | 101.36 | 103.92 | 103.90 | 109.00 |
| S-(1) (SK608-20.1) 10mg/kg (Q2Dx4) | 100.00 | 103.22 | 100.91 | 96.90 | 94.56 | 98.64 | 100.50 | 107.43 |
| S-(1) (SK608-20.1) 12mg/kg (Q2Dx4) | 100.00 | 102.39 | 97.75 | 91.08 | 87.61 | 87.86 | 93.43 | 100.53 |
| S-(1) (SK608-20.1) 14mg/kg (Q2Dx4) | 100.00 | 102.10 | 91.46 | 81.99 | 72.63 | 85.13 | 92.37 | 100.93 |

FIG. 4C

| % TGI | % BW LOSS | LCK |
|-------|-----------|-----|
| 77% | 15% | 1.0 |

| % TGI | TD | LCK |
|-------|-----|-----|
| 52% | 3/8 | 1.5 |

| % TGI | % REGRESSION | LCK | TD |
|---|---|---|---|
| 91% | 41% | 0.8 | 3/8 |

| % TGI | % REGRESSION | LCK |
|-------|--------------|-----|
| 94% | 84% | 0.8 |

| | % TGI | % BW LOSS | TD | LCK |
|---|---|---|---|---|
| | 0 | 0 | 0 | 0 |
| | 80% | 2% | 0 | 1.1 |
| | 97% | 23% | 2 | 2.0 |
| | 94% | 25% | 4 | 1.0 |
| | 88% | 13% | 2 | 1.0 |

FIG. 9B

Legend:
- CONTROL, VEHICLE 0.2mL (Q4Dx3)
- PACLITAXEL A3005-98-0002 36mg/kg (Q4Dx3)
- DOCETAXEL 1213299 24mg/kg (Q4Dx3)
- ABRAXANE 141361 & 20042 100-75mg/kg (Q4Dx3)
- S-(1) SY586-117FP#2 24mg/kg (Q4Dx3)

FIG. 9A

| % TGI | % BW LOSS | % REGRESSION | LCK | CURES |
|---|---|---|---|---|
| 0 | 3% | 0 | 0 | 0 |
| 93% | 15 | 76% | 2.8 | 1 |
| 93% | 21% | 72% | 3.0 | 0 |
| 96% | 0 | 82% | 3.0 | 0 |
| 81% | 20% | 14% | 1.3 | 0 |

CONTROL, VEHICLE 0.2mL (Q4Dx3)

PACLITAXEL A3005-98-0002 36mg/kg (Q4Dx3)

DOCETAXEL 1213299 24mg/kg (Q4Dx3)

ABRAXANE 200429 75mg/kg (Q4Dx3)

S-(1) SY586-117-FP#2 24mg/kg (Q4Dx3)

| % TGI | % BW LOSS | TD | LCK | CURES |
|---|---|---|---|---|
| 0 | 0 | 0 | 0 | 0 |
| 80% | 3% | 0 | 1.0 | 0 |
| 77% | 16% | 0 | 1.4 | 0 |
| 87% | 14% | 5/8 | NC | 1/8 |
| 68% | 17% | 3/8 | 0.9 | 0 |

| % TGI | % BW LOSS | % REGRESSION | TD | CURES | LCK |
|---|---|---|---|---|---|
| 0 | 0 | 0 | 0 | 0/8 | 0 |
| 99% | 1% | 76% | 0 | 3/8 | 2.1 |
| 97% | 15% | 59% | 0 | 1/8 | 2.7 |
| 98% | 4% | 72% | 1/8 | 0/8 | 2.3 |
| 89% | 13% | 0 | 0 | 0/8 | 1.3 |

Legend:
- ◆ CONTROL, VEHICLE 0.2mL (Q4Dx3)
- □ PACLITAXEL PA-051101 36mg/kg (Q4Dx3)
- △ DOCETAXEL 1213299 20mg/kg (Q4Dx3)
- ✳ ABRAXANE 200533 75mg/kg (Q4Dx3)
- ✻ S-(1) SY586-117-FP#2 20mg/kg (Q4Dx3)

| % TGI | % BW LOSS | LCK |
|-------|-----------|-----|
| 0 | 1% | 0 |
| 11% | 2% | 0 |
| 14% | 15% | 0.1 |
| 24% | 17% | 0.2 |

| % TGI | % BW LOSS | LCK |
|---|---|---|
| 0 | 12% | 0 |
| 22% | 3% | 0.2 |
| 23% | 17% | 0.2 |
| 41% | 13% | 0.4 |
| 51% | 14% | 0.4 |
| 55% | 20% | 0.5 |

CONTROL 200ul; 500ul (D1, 5, 9; D1, 4, 8, 11)

AVASTIN 5mg/kg (D1, 4, 8, 11)

S-(1) 24mg/kg (D1, 5, 9)

S-(1); AVASTIN 24mg/kg; 5mg/kg (D1, 5, 9; D2, 6, 10, 12)

AVASTIN; S-(1); 5mg/kg; 24mg/kg (D1, 4, 8, 11; D2, 6, 10)

S-(1); AVASTIN 24mg/kg; 5mg/kg (D1, 5, 9; D1, 4, 8, 11)

BIOLOGICALLY ACTIVE TAXANE ANALOGS AND METHODS OF TREATMENT BY ORAL ADMINISTRATION

CROSS-REFERENCE TO RELATED APPLICATIONS

This application is a continuation of U.S. patent application Ser. No. 17/539,578, filed Dec. 1, 2021, now granted as U.S. Pat. No. 11,873,308, which is a continuation of U.S. patent application Ser. No. 16/929,719, filed Jul. 15, 2020, now granted as U.S. Pat. No. 11,220,512, which is a continuation of U.S. patent application Ser. No. 16/569,302, filed Sep. 12, 2019, now granted as U.S. Pat. No. 10,745, 408, which is a continuation of U.S. patent application Ser. No. 15/797,145, filed Oct. 30, 2017, now granted as U.S. Pat. No. 10,450,323, which is a continuation of U.S. patent application Ser. No. 13/950,316, filed Jul. 25, 2013, now granted as U.S. Pat. No. 9,802,951, which is a continuation of U.S. patent application Ser. No. 13/620,852, filed Sep. 15, 2012, now granted as U.S. Pat. No. 8,552,056, which is a continuation of U.S. patent application Ser. No. 12/873,477, filed Sep. 1, 2010, now granted as U.S. Pat. No. 8,273,789, which is a continuation of U.S. patent application Ser. No. 12/593,153, which is now abandoned, which is 371 U.S. National Stage of PCT/US2008/055384, filed Feb. 28, 2008, now expired, which claims priority to and claims the benefit of U.S. Provisional Application No. 60/908,459, filed Mar. 28, 2007, and U.S. Provisional Application No. 60/911,607, filed Apr. 13, 2007, all of which are incorporated herein by reference in their entireties.

The present invention relates to a novel chemical compound for use in the treatment of cancer, to compositions containing said compound, methods of manufacture and combinations with other therapeutic agents.

Various taxane compounds are known to exhibit anti-tumor activity. As a result of this activity, taxanes have received increasing attention in the scientific and medical community, and are considered to be an exceptionally promising family of cancer chemotherapeutic agents. For example, various taxanes such as paclitaxel and docetaxel have exhibited promising activity against several different varieties of tumors, and further investigations indicate that such taxanes promise a broad range of potent anti-leukemic and tumor-inhibiting activity. One approach in developing new anti-cancer drugs is the identification of superior analogs and derivatives of biologically active compounds. Modifications of various portions of a complex molecule may lead to new and better drugs having improved properties such as increased biological activity, effectiveness against cancer cells that have developed multi-drug resistance (MDR), fewer or less serious side effects, improved solubility characteristics, better therapeutic profile and the like.

International Patent Application WO 2005/030150 discloses a series of taxane analogues useful for the treatment of cancer as well as methods of producing them. Other taxanes are described in EP 1 228 759; EP 1 285 920; EP 1 148 055; WO 01/56564; WO 01/57027; WO 94/10996; FR 2 715 846; U.S. Pat. No. 5,352,806; FR 2 707 293; WO 94/08984; WO 92/09589; WO 94/20485; WO 93/21173; Klein L L, "*Synthesis of 9-Dihydrotaxol: a novel bioactive taxane*", Tetrahedron letters, vol. 34, no. 13, 1993, pages 2047-2050; Datta A et al, "*Synthesis of novel C-9 and C-10 modified bioactive taxanes*", Tetrahedron letters, vol. 36, no. 12, 1995, pages 1985-1988; Klein L L et al, Journal of Medicinal Chemistry, no. 38, 1995, pages 1482-1492; J Demattei et al, "*An efficient synthesis of the taxane-derived anticancer agent abt-271*", Journal of Organic Chemistry, vol. 66, no. 10, 2001, pages 3330-3337; Gunda I Georg et al, "*The chemistry of the taxane diterpene: stereoselective reductions of taxanes*", Journal of Organic Chemistry, vol. 63, no. 24, 1998, pages 8926-8934. However, apart from paclitaxel and dodetaxol, no taxane has received regulatory approval to be marketed for use as an anticancer agent and no taxane has received regulatory approval to be marketed for use by oral administration. WO 2005/03150 and US Application No 2005/0148657 A1 disclose taxane analogues and derivatives possessing a $9\alpha$, $10\alpha$ configuration and an acetal or ketal bridge between the hydroxyl groups at the 7- and 9-positions. Synthesis of taxane analogues is also disclosed in WO 2007/073383, WO 2007/126893 and WO 2007/075870.

Zamir et al, Tetrahedron Letters, 37, 6435-6438 (1996) discloses taxane analogues containing a five membered A-ring and a position 1 $C(CH_3)_2OH$ group. These analogues were abeo-taxanes lacking the four membered oxatane ring. The compounds possessed a $10\beta$-, stereochemistry. No anti-cancer activity was ascribed to the compounds. Zamir et al, Tetrahedron Letters, 53. 15991-16008 (1997) discloses abeo-taxane analogues and also trapped intermediates containing a 5 membered A-ring and a position 1 $C(CH_3)_2OH$ group. The compounds possessed a $10\beta$-stereochemistry and an acetoxy group at position 13. Numerous structural analogues were disclosed but no biological data was provided on any compound. Wahl et al, Tetrahedron, 48, 6965-6974 (1992) discloses a wide range of modified taxane analogues including one which had a 5 membered A-ring and a 1 position $C(CH_3)_2OH$ group. The compound has a $10\beta$- hydroxyl group and a 9-keto group and was said to be active in the tubulin disassembly assay although no data was provided. Other publications relating to taxane analogues include Hue et al, Magn. Reson Chemis, 45, 527-530 (2007); Nicolaou et al, Ang. Chem. Int. Ed. 44, 1012-1044 (2005); Zamir et al, Tetrahedron Letters, 40, 7917-9920 (1999); Torregiani et al, Gaz. Chim. Italiana, 126, 809-814 (1996); Appendino et al, J. Chem. Soc. Comm., 1587-1589 (1993); and Samaranayake et al, J. Org. Chem., 56, 5114-5119 (1991). There is a need in the field of anti-cancer therapy for new therapeutic agents having improved pharmacological properties, such as increased biological activity (efficacy), effectiveness against cancer cells having multi-drug resistance (MDR), fewer or less serious side effects, improved solubility characteristics, better therapeutic profile and the like. Of particular need is the development of drugs having improved MDR reversal properties. There is also a need for methods of treating patients with such compounds in cancer treatment regimens. Many anti-cancer drugs currently available have utility against only a limited number of cancer cell-lines and there is therefore a need for new treatments that have utility against a wider range of cancers and specifically against those cancers which are currently difficult to treat or for which no appropriate therapy is available.

It is also the case that the majority of anti-cancer drugs must be administered by infusion or injection, and there exists a need for drugs that can be more readily administered to patients, in particular, orally. Furthermore, an ideal drug candidate will exist in a physical form that is stable, non-hygroscopic and easily formulated. The present invention is directed to meeting these needs, among other needs as disclosed herein.

Accordingly, the present invention provides a compound as a single diastereoisomer of the formula S-(1):

Formula S-(1)

In another aspect the present invention also provides a pharmaceutical composition comprising a compound of formula S-(1) as herein described together with a pharmaceutically acceptable diluent or carrier. The compound and compositions of the present invention have utility in the treatment of cancer. In another aspect of the invention therefore is provided the compound and compositions of the invention for use in the treatment of cancer. The present invention provides a method of treating cancer in a patient comprising administering to the patient a composition comprising the compound of the invention as hereinbefore described.

As used herein, the terms "taxane," "taxanes," "taxane derivatives" or "taxane analogs" and the like, include the diterpenes produced by the plants of the genus *Taxus* (yews), and may be derived from natural sources, may be prepared synthetically or may be obtained from semi-synthetic methods or a combination thereof. Such taxanes include paclitaxel and docetaxel that have a 6-membered A ring, as well as the abeo-taxanes that have a 5-membered A ring, as known in the art and as disclosed herein. The acid catalyzed rearrangement from the 6 membered A ring (and 8 membered B ring) to the 5 membered A ring (and 7 membered B ring) of the abeo taxane has been described for other taxane compounds, for example, in L. O. Zamir et al, Tetrahedron Letters, 40 (1999) 7917-7920, L. O. Zamir et al, Tetrahedron, Vol. 53, No. 47, 15991-16008 (1997), L. O. Zamir et al, Vol. 37, No. 36, 6435-6438 (1996), A. Wahl et al, Tetrahedron, Vol. 48, No. 34, 6965-6974 (1992), G. Appendino et al, J. Chem. Soc., Chem. Commun. 1587-1589 (1993), and G. Samaranayake et al, J. Org. Chem. 1991, 56, 5114-5119. The nomenclature used in these publications to name the rearranged 5 membered A ring structures has been 11(15→1) abeo-taxanes.

The term "baccatin" or "baccatin derivatives" means the taxane derivatives in which the side chain at the 13-position of the taxane skeleton is a hydroxy group and these derivatives are often referred to in the literature as a baccatin or "baccatin I-VII" or the like depending, on the nature of the substituents on the tricyclic rings of the taxane skeleton.

The term "subject" as used herein refers to an animal, preferably a mammal, most preferably a human.

The term "brain cancer" or "brain tumor" refers to any tumor that grows in the brain, including, but not limited to, astrocytoma, craniopharyngioma, glioma, ependymoma, neuroglioma, oligodendroglioma, glioblastoma multiforme, meningioma, medulloblastoma and other primitive neuroectoderma.

"Therapeutically effective amount" or an "effective amount" means a drug or composition of the present application that elicits any of the biological effects as listed in the present specification.

Brain disease further refers to cancers which have metastasized to the brain.

Pharmaceutically acceptable excipient, diluent, carrier or salt as used herein, means the excipient, diluent, carrier or salt of the compounds disclosed herein, that are pharmaceutically acceptable and provides the desired pharmacological activity.

Pharmaceutically acceptable salts of the compound of formula S-(1) comprise base salts thereof. Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. Hemisalts of bases may also be formed, for example, hemisulphate and hemicalcium salts. For a review on suitable salts, see *Handbook of Pharmaceutical Salts: Properties, Selection, and Use* by Stahl and Wermuth (Wiley-VCH, Weinheim, Germany, 2002).

Purity of diastereoisomers relates to the amount of a particular diastereoisomer that is present with respect to other diastereoisomers.

International Patent Application Nos. WO 2005/030150 and WO 2007/126893 and US Patent Application Nos. US 2005/148657 and US 2007/225510 disclose processes which lead to the preparation of the compound of formula (I), although the structural formula was not provided.

Formula (1)

This compound consists of a mixture of compounds of formula S-(1) and R-(1):

S-(1)

and

-continued

R-(1)

In attempting to separate these diastereoisomers, it was discovered that standard scale up chromatographic methods for the purification and separation of isomers using silica gel of various grades, from 28-200 mesh, 100-200 mesh, and Davisil® grade 633, 200-425 mesh, C-18 reversed phase media and attempted crystallization with various solvents compositions and solvent mixtures did not provide efficient separation of the diastereomeric mixture. Solvents such as hexanes, ethyl acetate, methyl tert-butyl ether, ethanol, acetone and their mixtures in different ratios and compositions were determined to be ineffective for the separation of each of the diastereoisomers from each other. It was surprisingly discovered that a solvent composition of 40% MTBE in heptane gave indication of separation of the diastereoisomers on a silica HPTLC plate with concentration zone with the compound of formula S-(1) showing an Rf~0.15. Based upon this observation, it was elected to attempt a normal phase chromatographic separation of the diastereoisomers by normal phase column chromatography. Having succeeded in separating the diastereoisomers it was surprisingly discovered that the compound of formula R-(1) had better solubility properties than the compound of formula S-(1) which is an important beneficial property in taxane cancer drugs.

It was surprisingly discovered that the compound of formula S-(1) possessed biological properties that were not obvious in light of those of the mixture of diastereoisomers identified as formula (1). After having separated and identified the individual diastereoisomers it was surprisingly discovered that the S-(1) diastereoisomer was significantly more active than the diastereomeric mixture. It is therefore preferable to use this diastereoisomer even though the R-(1) diastereoisomer has better solubility properties.

The pancreas can be divided into two parts: the exocrine and endocrine pancreas. About 95% of pancreatic cancers begin in the exocrine pancreas. The rest are cancers of the endocrine pancreas, which are also called islet cell cancers. Accordingly the compound and compositions of the present invention have utility in the treatment, preferably oral treatment, of these cancers.

In the brain, the design and development of effective anti-tumor agents for treatment of patients with malignant neoplasms of the central nervous system have been influenced by two major factors: 1) the drugs given at high systemic levels are generally cytotoxic; and 2) the blood-brain barrier provides an anatomic obstruction, limiting access of drugs to these tumors. Accordingly, one problem posed by the blood-brain barrier is that, in the process of protecting the brain, is that it excludes many potentially useful therapeutic agents.

The chemotoxic effect of taxanes, such as paclitaxel, is a result of the ability to inhibit cellular mitosis. Paclitaxel acts by binding to the β-subunit of polymerized tubulin, promoting the assembly of microtubules and inhibiting the normal dynamics of tubulin assembly necessary for mitosis. Resistance to taxanes is associated with the expression of the MDR 1 gene encoding P-gp, an ATP-dependent drug efflux pump that transports paclitaxel, other taxanes and other cytotoxic agents out of cells. The compound of formula S-(1) according to the present invention is a novel taxane analog, which achieves mutant-β-tubulin binding. In addition the compound of the invention, unlike paclitaxel, is not a substrate for the MDR protein. Modulation of the P-glycoprotein, whose substrates are actively pumped out of brain cells into capillary lumens, has been found to facilitate the delivery of drugs to the brain. As demonstrated by the experiments described herein, the compound of formula S-(1) freely crosses the blood-brain barrier and has activity against brain tumors.

Surprisingly, in xenograft models, the compound of formula S-(1) has been shown to be active as an antitumor agent against xenografts, regardless of whether such xenografts express the P-gp pump. In addition to this anti-resistance activity, the compound of formula S-(1) also appears to have a number of advantages over traditional taxanes, including activity in brain tumors, pancreatic tumors, and oral bioavailability.

Furthermore, as shown in Table 1, the compound of formula S-(1) was determined to be significantly more active than the diastereoisomer of formula R-(1) in a number of cytotoxicity assays as measured by MTS proliferation assay.

TABLE 1

| MTS Proliferation Assay Results | | |
| --- | --- | --- |
| | | nM IC$_{50}$ |
| Cancer Type & Cell line | S-(1) | R-(1) |
| Neuroblastoma SKNAS | 11 | 80 |
| head/neck FADU | 21 | 96 |
| prostate DU145 | 60 | 212 |
| breast MDA435s | 10 | 52 |
| head/neck KB | 9.4 | 37.7 |
| head/neck KBV (MDR+) | 553 | 1196 |
| colon HT29 | 0.006 | 1.6 |
| uterine MESSA | 2.9 | 7.8 |
| uterine MESSA/Dox (MDR+) | 44.8 | 233 |
| prostate PC-3 | 0.03 | 2.5 |

In one embodiment of the present invention there is provided the compound of formula S-(1) as a single diastereoisomer as shown below. Also provided herein are novel methods for the preparation of S-(1), pharmaceutical compositions comprising S-(1) and methods of treating cancer comprising administering such a pharmaceutical composition to a patient in need thereof.

S-(1)

In a preferred embodiment the compound is isolated as a pure diastereoisomer. Preferably the isolated compound is greater than 95% pure. More preferably the compound is greater than 99% pure. Preferably, therefore, the present invention encompasses the compound of formula S-(1) as a single diastereoisomer having a diastereomeric excess (d.e.) of at least 80%, preferably at least 90%, more preferably at least 95%, yet more preferably at least 98% and most preferably at least 99%. In particular, the compound of the invention comprises less than 5% of the diastereoisomer of formula R-(1), preferably less than 3%, more preferably less than 2%, yet more preferably less than 1% and most preferably less than 0.5%.

R-(1)

Additionally, the compound of the present invention comprises less than 5% of the compound of formula (2), preferably less than 3%, more preferably less than 2%, yet more preferably less than 1% and most preferably less than 0.5%.

Formula (2)

In another aspect of the invention there is provided a pharmaceutical composition comprising the compound of formula S-(1) as herein defined in combination with a pharmaceutically acceptable diluent or carrier. Additionally, the compound of formula S-(1) as herein defined may be administered orally. The invention therefore also provides a pharmaceutical composition for oral administration comprising the compound of formula S-(1) as herein defined in combination with a pharmaceutically acceptable diluent or carrier. Additionally, the compound of formula S-(1) as herein defined may be administered parenterally, such as by intravenous injection or infusion. The invention therefore also provides a pharmaceutical composition for parenteral administration comprising the compound of formula S-(1) as herein defined in combination with a pharmaceutically acceptable diluent or carrier.

In another aspect there is provided a method for the treatment of cancer in a patient comprising administering to the patient a therapeutically effective amount of the compound of formula S-(1) as herein defined to a patient in need of such treatment. The compound of the present invention may be used in the treatment of diseases mediated by tubulin. The cancer may be selected from the group consisting of brain, hepatocellular, sarcoma, leukemia, lymphoma, and other bone marrow dyscrasias, neuroblastoma, glioblastoma, cervical, colorectal, pancreatic, renal, thyroid, lung, small-cell lung, non-small cell lung, gastric, breast, ovarian, prostate, head and neck and melanoma. In one preferred embodiment the cancer is colorectal cancer. In another preferred embodiment the cancer is pancreatic cancer. In another preferred embodiment the cancer is prostate cancer. In yet another preferred embodiment the cancer is brain cancer. In a most preferred embodiment the cancer is neuroblastoma or glioblastoma.

The present application provides pharmaceutical compositions comprising a diasteroisomer of the formula S-(1) in which the isomer is greater than 90% pure, greater than 95% pure, greater than 97% pure, greater than 99% pure or greater than 99.5% pure. The present invention additionally comprises compounds useful as intermediates in processes for the preparation of the compound of formula S-(1).

In one embodiment of the present invention there is provided the compound of formula S-(34) as a single diasteroisomer as shown below. Also provided herein are novel methods for the preparation of S-(34).

S-(34)

Preferably, the present invention encompasses the compound of formula S-(34) as a single diastereoisomer having a diastereomeric excess (d.e.) of at least 80%, preferably at least 90%, more preferably at least 95%, yet more preferably at least 98% and most preferably at least 99%.

In particular, the compound of the invention comprises less than 5% of the diastereoisomer of formula R-(34), preferably less than 3%, more preferably less than 2%, yet more preferably less than 1% and most preferably less than 0.5%.

R-(34)

Processes

Methods for the preparation of the compound of formula (1) are described in International Patent Applications WO 2005/030150 and WO 2007/126893. Although the structure was not provided these processes lead to its preparation.

Definitions

CSA: Camphorsulfonic Acid
DCC: N,N'-Dicyclohexyl-Carbodiimide
10-DAB III: 10-Deacetylbaccatin III
DCM: Dichloromethane
DMAP: Dimethylaminopyridine
DMSO: Dimethylsulfoxide
Hr: Hour
HPLC: High Performance Liquid Chromatography
IPAc: Isopropyl Acetate
LCMS: Liquid Chromatography Mass Spectrometry
MTBE: Methyl tert-Butyl Ether
4-PP: 4-Pyrrolidinopyridine
TEA: Triethylamine
TES-Cl: Triethylsilyl Chloride
THF: Tetrahydrofuran
TPAP: Tetrapropyl Ammonium Perruthenate
TPAP: Tetrapropyl Ammonium Perruthenate A method for synthesizing the compound of formula (3) is shown below with reference to Scheme 1. 10-Deacetyl-baccatin III (10-DAB III), which has formula (4) as shown in Scheme 1, is a commercially available (Sigma-Aldrich) compound used as an intermediate in the preparation of various taxanes.

Scheme 1

4

-continued

11

-continued

13

3

4

5 acetal formation → protection →

Coupling →

6

7

Deprotection →

8

TES protection →

12

-continued

9

Oxidation →

10

Reduction NaBH₄ →

11

Acetylation →

12

Deprotection →

13

Acetal Formation →

3

In this process, 10-DAB III, formula (4), is first protected at both the C-7 and C-10 positions to form the C7, C10 di-CBZ derivative of formula (5). 10-Deacetylbaccatin III of formula (4) (50 g, 91 mmol) was dissolved in THF (2 L, 40 ml/g) by warming to 40° C. in a warm-water bath. The solution was cooled to −41° C. in a Neslab chiller and benzylchloroformate (46 mL, 3.2 eq, 294 mmol) was added to the stirred chilled solution followed by further cooling to −44° C. To this solution 2.3M hexyl lithium solution (130 mL, 3.3 eq, 303 mmol) was added gradually over 45 min while maintaining the temperature of the reaction mixture at ≤−39° C. Stirring was continued in the Neslab for 45 minutes at which time HPLC indicated the reaction had gone to completion. At two hours total reaction time, the reaction was quenched by the addition of TN HCl (400 mL) and IPAc (1 L) and removal from the Neslab chiller. The reaction was allowed to stir while warming to 10° C. The layers were separated and the IPAc layer was washed sequentially with $H_2O$ (500 mL), saturated $NaHCO_3$ (200 mL) and $H_2O$ (4×500 mL) and then filtered through a silica gel pad. The filtrate was concentrated until solids started to form. IPAc (850 mL) was added and the mixture was heated to 60° C. to dissolve some of the solids. To the warm solution, heptanes (800 mL) were added and the solution was cooled in the refrigerator and filtered. The solids collected by the filtration were washed with heptanes and dried under vacuum at 45° C. to give formula (5).

Next, the compound of formula (5) was coupled with a side chain to form the compound of formula (7). Here, the side chain of the compound of formula (6), (38 g, 99.6 mmol) was dissolved in toluene to a known concentration (0.0952 g/mL). This solution was added to the compound of formula (5) (54.0 g, 66.4 mmol). The solution was heated in a warm-water bath and DMAP (8.13 g, 66.4 mmol) and DCC (25.3 g, 120 mmol) in toluene (540 mL) were added to the warm reaction mixture. While maintaining the temperature at about 51° C., the reaction was continually stirred and sampled periodically for HPLC. After 3 hours, additional DCC (13.0 g) in toluene (140 mL) was added. The following morning (25.25 hr), MTBE (450 mL) was added and the reaction mixture was filtered through a pad of silica gel, washed with MTBE followed by ethyl acetate, and concentrated to give the compound of formula (7) as 61.8 g of an oil.

The compound of formula (7) was then deprotected at both the C7 and C10 positions to give the compound of formula (8). A solution of THF (300 mL) and HCl (22 mL) was added to a solution of the compound of formula (7) (61.8, 52.5 mmol) in THF (15 mL/g, 920 mL). The resulting solution was flushed with nitrogen. A catalyst (10% Pd/C with 50% water, 99.1 g) was added and the flask was flushed with nitrogen three times and then with hydrogen three times. The reaction mixture was stirred vigorously under a hydrogen balloon for 21 hours. At this time the reaction was sampled and HPLC indicated that 38% by area of starting material still remained. Water (10 mL) was added and stirring continued. Twenty hours later, HPLC indicated the same amount of starting material still remaining. The reaction mixture was filtered through celite and washed with THF. It was then concentrated to remove excess THF; fresh catalyst (101 g) was added and the reaction mixture was placed back under hydrogen as before. After another 24 hours, an intermediate compound was still present and still more catalyst (20 g) was added. After another hour, HPLC indicated that the reaction was complete. The reaction mixture was filtered through celite and washed through with IPAc. The combined filtrate was washed with $NH_4Cl$ solution (500 mL), water (500 mL), 5% $NaHCO_3$ (500 mL), $H_2O$ (300 mL), and brine (300 mL). The organic layer was dried, filtered, and concentrated to give a foam of the compound of formula 38 (42.5 g).

The compound of formula (8) was then converted to the compound of formula (9). Formula (8) (41.4 g, 52.5 mmol) was dissolved in DCM (500 mL) at room temperature. In the case that the impurity was water, $Na_2SO_4$ was added to the solution, and the solution was filtered through filter paper into to a 2 L flask. The solids were collected and washed with DCM (250 mL) and the washings transferred into the flask. The flask was covered with a septum and $N_2$ balloon. TEA (35 mL) followed by DMAP (1.28 g) and TES-Cl (~30 mL, 3.5 eq) were added to the solution and stirred. Additional TES-Cl (15 mL) and TEA (20 mL) were added, and after 6 hours HPLC indicated the reaction had gone to completion.

The reaction was then quenched by the addition of ethanol (25 mL). The layers were separated and the organic layer was washed with saturated $NH_4Cl$ (~500 mL). The organic layer was dried over $Na_2SO_4$ and concentrated. A flash column was packed with silica gel and wet with 8:2 heptane/IPAc (1.5 L). The solids were dissolved in 8:2 heptane/IPAc (250 mL) and filtered to remove solids that would not dissolve. This solution was concentrated to ~100 mL and applied to the column. The column was eluted with 8:2 heptane/IPAc and fractions collected. Fractions with product were pooled and concentrated to give foam of formula (9) (24.5 g).

The compound of formula (9) was then oxidized to form the compound of formula (10). Here, solid $Na_2SO_4$ was added to a solution of formula (9) (24.5 g, 24.0 mmol) and 4-methyl morpholine N-oxide (10.1 g, 84 mmol) in DCM (340 mL) to assure that the reaction was dry. The mixture was stirred for 1 hour and then filtered through 24 cm fluted filter paper into a 2 L 3-neck round bottom flask. The $Na_2SO_4$ solids were washed with DCM (100 mL) and the washings transferred into the flask. Molecular sieves (6.1 g, 0.15 g/g) were added to the solution and stirring was begun. TPAP (1.38 g) was added and the reaction was allowed to stir under a $N_2$ blanket. Samples were taken periodically for HPLC. Additional TPAP (0.62 g) was added after 2 hours and again (0.8 g) after 15 hours. The reaction mixture was applied to a pad of silica gel (86 g), wet with 8:2 heptane/IPAc and eluted with IPAc. The fractions were collected, pooled and concentrated to an oil. 4-Methyl morpholine N-oxide (5.0 g) and DCM (100 mL) were added and stirred. $Na_2SO_4$ (13 g) was added to the mixture and it was filtered through filter paper. The $Na_2SO_4$ solids remaining in the filter was washed with DCM (45 mL). Molecular sieves (5 g) and TPAP (1.03 g) were added to the solution and after 45 minutes, more TPAP (1.05 g) was added. A pad of silica gel was prepared and wet with 80:20 Heptane/IPAc. The reaction mixture was applied to the pad and eluted with IPAc. Fractions were collected and those fractions containing product were pooled and concentrated to give an oil product of formula (10) (21.8 g). Next, the compound of formula (10) was reduced to form the compound of formula (11). $NaBH_4$ (365 mg, 6 eq) was added to a stirred solution of formula (10) (1.6 g) in ethanol (19 mL) and methanol (6.5 mL) cooled in an ice-water bath. After 1 hour, the reaction mixture was removed from the ice-water bath and at 2 hours, the reaction was sampled for HPLC, which indicated the reaction had gone to completion. The reaction mixture was cooled in an ice-water bath and a solution of $NH_4OAc$ in methanol (15 mL) was added followed by the addition of IPAc (50 mL) and $H_2O$ (20 mL). It was mixed and separated. The organic layer was washed with water (20 mL) and brine (10 mL), a second time with water (15 mL) and brine (10 mL), and then twice with water (2×15 mL). It was dried over $Na_2SO_4$ and placed in the freezer overnight. The following morning a sample was taken for HPLC and the reaction was dried and the organic layer was concentrated on the rotary evaporator. It was placed in the vacuum oven to give a foam product of formula (11) (1.45 g).

The compound of formula (11) was then acylated to form the compound of formula (12). TEA (5.8 mL, 41.5 mmol), Ac$_2$O (2.62 mL, 27.7 mmol) and DMAP (724 mg, 5.5 mmol) were added to a solution of formula (11) (14.1 g, 13.8 mmol)) in DCM (50 mL). The reaction was stirred and sampled for HPLC periodically. After 18.5 hours, additional TEA (1.5 mL) and Ac$_2$O (1 mL) were added. At 19 hours, HPLC indicated the reaction had gone to completion. The reaction mixture was diluted with IPAc (300 mL) and poured into 5% NaHCO$_3$ (100 ml). It was then stirred, separated, and the organic layer was washed with water (100 mL), saturated NH$_4$Cl (2×100 mL), water (3×50 mL) and brine (50 mL) and then filtered through Na$_2$SO$_4$. The mixture was concentrated to give a foam product of formula (12) (14.6 g).

Next, the compound of formula (12) was converted to the compound of formula (13). A quantity of formula (12) (3.0 g, 2.83 mmol) was weighed into a 100 mL flask. Next, DCM (24 mL) followed by methanol (6 mL) were added to the flask at room temperature. Stirring of the mixture began under N$_2$ and camphorsulfonic acid (CSA) (0.0394 g, 0.17 mmol) was added. After 4 hours LCMS indicated the product had formed. 5% NaHCO$_3$ (15 mL) was added to the reaction mixture; it was shaken vigorously and then transferred to a separatory funnel. The reaction flask was rinsed into the separatory funnel with 5% NaHCO$_3$ (25 mL) and, thereafter, the reaction mixture was shaken and the layers were separated. The organic layer was washed with brine, dried over Na$_2$SO$_4$, and concentrated. MTBE (3×25 mL) was added and the reaction mixture was concentrated to dryness after each addition to finally give 3.71 g foam. The foam was dissolved in MTBE (10 mL) and stirred. Heptane (50 mL) was slowly added to the reaction solution and solids began to form immediately. The solids were vacuum filtered and rinsed with heptane (720 mL). The solids were collected and dried in a vacuum oven at 40° C. to give the compound of formula (13) (2.18 g).

The compound of formula (13) was then converted to the compound of formula (3). A solution of formula (13) (2.1 g, 2.52 mmol) in DCM (10.5 mL) was stirred at room temperature. Next, 3,3-dimethoxy-1-propene (2.03 g, 17.7 mmol) followed by CSA (0.035 g, 0.15 mmol) were added to the solution. After the solution was stirred for 3.5 hours, LCMS indicated the reaction had gone to completion. The reaction was diluted with DCM (25 mL) and added to a separatory funnel with 55 mL 5% NaHCO$_3$ solution. The layers were separated and the aqueous layer was washed with DCM (25 mL). The two organic layers were combined, washed with brine, dried over Na$_2$SO$_4$ and concentrated. A flash chromatography column was packed with silica gel (230-400 mesh) and wet with 50:50 MTBE/heptane (1000 mL). The reaction mixture was dissolved in MTBE (10 mL), loaded on the column and eluted with 50:50 MTBE/heptane. The fractions were collected, pooled, concentrated and dried in a vacuum oven at 50° C. to give product of formula (3).

Scheme-1a

To a solution of the compound of formula (12) (0.500 g, 0.4716 mmol) in methanol, a −19° C. was added 0.2N HCl (1.2 equiv, 2.83 mL) slowly and stirred, The reaction was quenched by the addition of 5% sodium bicarbonate solution, after stirring the reaction for about 1 hr. The mixture was diluted with ethyl acetate and partitioned. The organic layer was washed with water, dried (Na$_2$SO$_4$) and roto-stripped to provide crude compound of formula (13a). The crude product was purified by normal phase flash chromatography eluting with 15% ethyl acetate in heptane followed by neat ethyl acetate to provide clean product compound of formula (13a) (0.235 g) To a solution of compound of formula (13a) (0.41 g) in DMF (N$_5$N-dimethylformamide) was added acroleindimethyl acetal (3,3-dimethoxy-1-pro-pene, 2 mL) followed by camphorsulfonic acid (0.1 g). The reaction mixture was heated at ~50° C. and monitored periodically by LC-MS analysis for progress of the reaction. The reaction was judged complete at about 3 hours and quenched by addition of 5% sodium bicarbonate solution. The reaction mixture was diluted with IPAc (isopropyl acetate, 20 mL) and water (20 mL). The mixture was shaken well and the organic layer partitioned. The aqueous layer was re-extracted twice with IPAc. The combined IPAc layers were washed with water and rotostripped to provide the crude product formula (3a) as a foam. A Kromasil column (100A, 50 cm×2.1 cm column) was conditioned with 65:35 n-heptane:waMTBE (1% water and 1% acetic acid in methyl-/−butyl ether). The crude compound of formula (3a) was loaded as a solution in toluene onto the Kromasil column and eluted with 65:35 n-heptane:waMTBE. The pure fractions containing the product were pooled, neutral-ized with ~50 mL of 5% sodium bicarbonate solution. The organic layer was partitioned and evaporated under reduced pressure and dried overnight in the vacuum oven at 40° C.

to provide the pure compound of formula (3a) as a white solid (~57 mg). The product was characterized by HPLC/LC-MS and high field multidimensional NMR spectroscopy. An alternative method for synthesizing the compound of formula (3) is shown below with reference to Schemes 2 to 4.

Scheme 2

14

15

16

17

18

19

-continued

20

14

15

16

17

18

19

-continued

20

As shown, paclitaxel of formula 14 is first protected at the 2'-hydroxyl with a hydroxyl protecting group such as tert-butyldimethylsilyl (TBDMS). To a 500 mL round bottom flask (RBF) equipped with a magnetic stir bar was charged 50.0 g (58.6 mmol) paclitaxel, formula 14, 14.0 g (205 mmol, 3.5 eq.) imidazole, and 26.5 g (176 mmol, 3.0 eq.) TBDMS-Cl. The flask was placed under a nitrogen environment and 350 mL (7 mL/g paclitaxel) anhydrous N,N-dimethyl formamide (DMF) was charged to the flask. The reaction was stirred at room temperature for twenty hours, then was worked up by diluting the reaction solution in 600 mL isopropyl acetate (IPAc) and washing with water until the aqueous wash reached pH 7, then with brin. The organic partition was dried over magnesium sulfate, filtered and then was evaporated to a white foam solid to yield 66.9 g (93.0 area percent) of unpurified 2'-O-TBDMS protected compound of formula 15.

Next, the 10-acetyl group is removed using methods known in the art, such as by hydrazinolysis. To a 1 L RBF equipped with a magnetic stir bar was charged 59.5 g compound 15 and 600 mL (10 mL/g) IPAc. The solution was stirred to dissolve compound 15, then 60 mL (1 mL/g) hydrazine hydrate was charged to the flask and the reaction stirred at room temperature for one hour. The reaction was worked up by diluting the reaction solution in 1.2 L IPAc and washing first with water, then ammonium chloride solution, then again with water until the aqueous wash was pH 7 and lastly with brine. The organic partition was dried over magnesium sulfate, filtered and evaporated to 55.8 g of solid. The solid was redissolved in 3:1 IPAc (1% water): heptane to a concentration 0.25 g/mL total dissolved solids (TDS) and purified on a YMC silica column; the column eluent was monitored for UV absorbance. The fractions were pooled based on HPLC analysis and evaporated to yield 39.3 g (98.6 area percent) of the 2'-O-TBDMS-10-deacetyl compound of formula 16.

The 7-hydroxyl is further protected with a protecting group such as triethylsilyl (TES). To a 500 mL RBF equipped with a magnetic stir bar was charged 39.3 g (42.5 mmol) compound 16 and 15.6 g (127 mmol, 3 eq.) 4,4-dimethylaminopyridine (DMAP). The flask was placed under nitrogen and 390 mL (10 mL/g) anhydrous dichloromethane (DCM) was charged to the flask to dissolve the solids followed by 14 mL (84.9 mmol, 2 eq.) TES-Cl. The reaction was stirred at room temperature for three hours. The reaction was worked up by evaporating the reaction solution to approximately half its starting volume and diluting it in 300 mL EtOAc and washing with water and dilute HCl solutions until the pH of the aqueous wash was approximately 7, then washing with brine. The organic partition was dried over magnesium sulfate and evaporated to yield 42.0 g (97.7 area percent) of white solid of formula 17.

Next, oxidation of the 10-hydroxyl yields a 9,10-diketo compound. To a 1 L RBF equipped with a magnetic stir bar was charged 41.0 g (39.4 mmol) of the compound of formula 17, 2.1 g (5.92 mmol, 0.15 eq.) of tetrapropylammonium perruthenate (TPAP), 13.9 g (118 mmol, 3 eq.) N-methyl-morpholine-N-oxide (NMO). The flask was placed under nitrogen and 720 mL (~20 mL/g) anhydrous DCM charged to the flask to dissolve the solids. The reaction was stirred at room temperature for 22 hours. The reaction was worked up by concentrating the reaction solution to half its volume and then drying the reaction contents onto 175 g silica gel (EM Sciences 40-63μ). The product containing silica was placed on 30 g of clean silica gel (EM Sciences 40-63μ) and the product eluted from the silica with 4 L methyl tert-butyl ether (MTBE). The MTBE was evaporated to yield 37.3 g (93.2 area percent) 2'-O-TBDMS-7-O-TES-9,10-diketo compound of formula 18.

Selective reduction of the 9,10-diketo compound yields the 9,10-α,α-hydroxy compound. To a 2 L RBF equipped with a magnetic stir bar was charged 37.3 g (35.9 mmol) protected 9,10-diketo compound of formula 18 and 900 mL (~30 mL/g compound 18) of 3:1 EtOH/MeOH. The solution was stirred to dissolve the solids then the flask was placed in an ice/water bath and the solution was stirred for 30 minutes. Then 8.1 g (216 mmol, 6 eq.) of sodium borohydride (NaBH₄) was charged to the flask and the reaction stirred in the ice/water bath for five hours. The reaction was worked up by diluting the reaction solution in 1 L IPAc and washing with 4×750 mL water, then with 200 mL brine. The organic partition was dried over magnesium sulfate. The aqueous washes were reextracted with 500 mL IPAc. The organic re-extract solution was washed with 100 mL brine then dried over magnesium sulfate and combined with the first organic partition. The IPAc solution was concentrated until solids began precipitating out then heptane was added to the solution to crystallize the product of formula 19. The crystallizing solution was placed in a freezer overnight. Three crystallizations were done on the material, the first yielded 4.1 g (95.3 area percent) product, the second yielded 18.3 g (90.9 area percent) product, and the third yielded 2.9 g (81.7 area percent) product. The original work on this reaction employed flash chromatography to purify the product. However, the crystallizations that were performed gave similar purity, by HPLC, to the chromatographed material from earlier work.

To a 25 mL RBF, equipped with a magnetic stir bar and under a nitrogen environment, was charged 300 mg (0.288 mmol) of the compound of formula 19, (0.720 mmol, 2.5 eq.) acid chloride (CH₃COCl), 140 μL (1.01 mmol, 3.5 eq.) triethyl amine (TEA), 13 mg (0.086 mmol, 0.3 eq.) 4-PP, and 10 mL anhydrous DCM. The reactions were stirred at room temperature for 15+ hours; reactions generally ran overnight and were monitored by TLC and/or HPLC in the morning for consumption of starting material. The reactions were worked up by diluting the reaction solution in 20 mL EtOAc and washing with water until the pH of the water washes was approximately 7. The organic solution was then washed with brine and dried over sodium sulfate before evaporating to dryness. The resulting product is the compound of formula 20.

When the reagent used is a carboxyl anhydride, an exemplary procedure is as follows. To a 25 mL RBF, equipped with a magnetic stir bar and under a nitrogen environment, was charged 300 mg (0.288 mmol) of the compound of formula 19, (2.88 mmol, 10 eq.) acid anhydride (CH₃COOCOCH₃), 106 mg (0.864 mmol, 3 eq.) DMAP, and 5 mL anhydrous DCM. The reactions were stirred at room temperature for 15+ hours. The reactions were worked up by adding 5 mL saturated sodium bicarbonate solution to the reaction flask and stirring for 5 minutes. The solution was then transferred to a separatory funnel and organics were extracted with 20 mL EtOAc. The organic extract was then washed with saturated sodium bicarbonate and water until the pH of the water washes was approximately 7. The organic partition was then washed with brine and dried over sodium sulfate before evaporating to dryness. The compound of formula 20 may be deprotected at the 2'- and 7-positions in either a two-step process or a single step. For example, as shown in Scheme 3, the 7-O-TES group may be removed from formula 20 to give formula 21 using acetonitrile (ACN) and aqueous HF.

-continued

22

To a 500 mL Teflon bottle equipped with a magnetic stir bar is charged 2.50 g (2.40 mmol) of the compound of formula 20 and 100 mL ACN. The bottle is placed in an ice/water bath and the solution stirred for 30 minutes. Next, 0.8 mL of 48% HF aqueous is added slowly to the reaction solution and the reaction stirred in the ice/water bath for 20 minutes. The reaction is monitored by TLC for disappearance of the starting material. The reaction is worked up by diluting the reaction solution by adding 200 mL EtOAc and quenching the acid by adding 25 mL saturated sodium bicarbonate solution to the bottle and stirring for 10 minutes. The solution is then transferred to a separatory funnel and the organic partition washed with water until the pH of the water wash is approximately 7, then washed with brine. The organic partition is dried over sodium sulfate and then evaporated to a solid of formula 21.

Next, the 2'-O-protecting group may be removed from formula 21 to give formula 22 as shown in Scheme 3. To a 50 mL Teflon bottle equipped with a magnetic stir bar was charged, 500 mg of the compound of formula 21 and 5 mL anhydrous THF. Next, 1 mL HF-pyridine solution was slowly charged to the reaction solution. The reaction was stirred at room temperature for 1 hour; reaction progress was monitored by TLC and/or HPLC for disappearance of starting material. The reaction was worked up by adding 10 mL EtOAc to the bottle to dilute the reaction solution and then saturated sodium bicarbonate was slowly added to the bottle to neutralize the HF. The solution was transferred to a separatory funnel and the organic partition was washed with 10 wt % sodium bicarbonate solution then water until the pH of the water wash was approximately 7. Then the organic partition was washed with brine and then dried over sodium sulfate before evaporating to a solid of Formula (22). Further, as indicated above, the 2'- and 7-positions of the compound of formula 20 may be deprotected in a one-step procedure using tetrabutylammoniumfluoride (TBAF) to directly produce formula 22. A 10 mL RBF equipped with a magnetic stir bar was charged with 100 mg of the compound of formula 20 and 5 mL EtOAc or THF to dissolve the taxane. Next, 100 μL of 1M TBAF in THF was charged to the flask and the reaction was stirred at room temperature for 1 hour; the reaction was monitored by TLC and/or HPLC for disappearance of starting material. The reaction was worked up by washing the reaction solution with water and then brine. The organic partition was dried over sodium sulfate and evaporated to a solid of formula 22. This method removes both the 2'-O-TBDMS protecting group and the 7-O-TES protecting group. As shown for example in Scheme 4, the compound of formula 22 may be protected as a 7,9-acetal, such as a cyclic acetal such as with anisaldehyde dimethyl acetal to form a compound of formula 23.

Scheme 3

US 12,583,865 B2

23
24
-continued

Scheme 4

22

7,9-protection

23 reductive
cleavage

24

+

25 coupling

26 i. deprotection
ii. N-boc
protection 27 and 28 acetal
formation

3

22

23

24

26

7,9
protection reductive
cleavage 25
coupling (i) deprotection
(ii) N-Boc
protection

25

-continued

27 & 28

To a 50 mL RBF was charged 1.15 g (1.35 mmol) of the compound of formula 22 and 25 mL anhydrous DCM, under nitrogen. 343 µL (2.02 mmol, 1.5 eq.) anisaldehyde dimethyl acetal was charged to the flask, followed by 51 mg (0.269 mmol, 0.2 eq.) p-toluenesulfonic acid (PTSA). The reaction was stirred at room temperature for 45 minutes then was worked up by extracting the product with EtOAc and washing with saturated sodium bicarbonate solution followed by water. The organic partition was evaporated to yield approximately 1.5 g of crude product. The crude product was purified by flash chromatography to yield 0.72 g of pure product of formula 23.

Next, the side chain is cleaved to form the compound of formula 24. To a 25 mL RBF was charged 720 mg (0.740 mmol) of the compound of formula 23 and 15 mL anhydrous THF, under nitrogen. The flask was placed in an ice/water/ammonium chloride, −13° C. bath. Solid lithium borohydride (29.0 mg, 1.33 mmol, 1.8 eq.) was charged to the reaction flask and the reaction stirred at −13° C. for two hours before raising the temperature to 0° C. The reaction was worked up after five hours fifteen minutes by diluting with EtOAc and washing with water and ammonium chloride solution. The organic partition was evaporated to yield 650 mg of crude compound but HPLC indicated that there was only approximately 20% product and mostly unreacted starting material; therefore, the reaction was restarted by repeating the above procedure and running the reaction for an additional six hours. The organic partition was evaporated to yield approximately 660 mg of crude product. The compound was purified on a spherical silica column to yield the compound of formula 24.

The compound of formula 24 is then coupled with formula 25 to provide the compound of formula 26. To a 5 mL RBF was charged 180 mg (0.255 mmol) of the compound of formula 24 and 105 mg (0.510 mmol, 2.0 eq.) DCC. Toluene (2 mL) was then added to dissolve the solids. Next, formula 28 (158 mg, 0.383 mmol, 1.5 eq.) was dissolved in 1.0 mL DCM and the solution was charged to the reaction flask followed by 6 mg (0.038 mmol, 0.15 eq.) 4-PP. The reaction was stirred at room temperature for 23 hours and then was quenched by adding 11.5 µL acetic acid and 4 µL water and stirring for one hour. MTBE was added to the reaction flask to precipitate DCU and the reaction solution was filtered to remove the precipitate. The filtrate was slurried with activated carbon then passed across a silica plug to remove the 4-PP salts. The eluent was evaporated to a solid to yield 271 mg of crude coupled product of formula 26.

The 7,9-acetal and N,O-acetal protecting groups may then be removed and an N-acyl group added to form the compounds of formula 27 and 28, which may be separated from each other by liquid chromatography or kept together for the next step. While the same anisaldehyde group is used at both the 7,9-acetal and N,O-acetal in the exemplary compound of formula 26, such that both groups may be removed in a single step, it should be appreciated that other acetal protecting groups are contemplated such that multiple deprotection steps may be required. To a 10 mL RBF was charged, 270 mg (0.245 mmol) of the compound of formula 26, 220 mg (0.8 g/g coupled ester) Degussa type palladium on carbon, and 4.1 mL THF. In a separate vial, 99 µL conc. HCl was diluted in 198 µL water and 1.0 mL THF. This solution was added to the reaction flask and the flask was sealed and placed under hydrogen. The hydrogenation reaction was stirred for 31 hours then was quenched by removing the hydrogen and filtering the catalyst from the reaction solution then adding 84.5 µL (0.368 mmol, 1.5 eq.) t-butoxy carbonyl (t-BOC) anhydride followed by 684 L TEA. The reaction stirred an additional 21 hours and then was worked up, diluting the filtrate with EtOAc and washing with water. The organic partition was evaporated to approximately 370 mg of oil. The oil was purified first by flash chromatography, then preparative TLC (PTLC) then by a semi-prep reverse phase column to yield 3.9 mg of pure product of formula 27 and 28.

A 7,9-acetal may then be formed to provide the compound of formula 3. In a HPLC vial insert, 3.4 mg (4.13 µmol) of the compounds of formula 27 and 28 was charged followed by 70 µL DCM. Next, 12.8 µL of a 1 to 20 diluted acrolein dimethyl acetal in DCM (0.64 µL acetal, 5.37 µmol, 1.3 eq.) was charged to the insert followed by 8.4 µL (0.413 µmol, 0.1 eq.) of a 0.05M PTSA solution in DCM. The reaction was lightly agitated then sat at room temperature. The reaction took more additions of the acetal solution to drive it to completion then was worked up after a couple of days by filtering the solution through approximately 80 mg of basic activated alumina. The alumina was washed with DCM then EtOAc and the fractions evaporated to dryness. The crude compound was purified on a normal phase analytical column to yield 605 µg of the compound of formula 3. The compound of formula 3 may then be separated into its individual diastereoisomers to produce the compound of formula S-(1) via chromatography using a solvent composition of 35% MTBE in heptane as described in the examples.

Scheme-4a 7,9 protection

22a

-continued

23a reductive
cleavage

24a 25
coupling

26a (i) deprotection
(ii) N-Boc protection

27a & 28a acetal formation

-continued

3

As generally described and specifically exemplified above, these processes may be performed with the isolation of one or more of the intermediate compounds, or the process may be performed without the isolation and purification at each and every single processing steps.

Standard procedures and chemical transformation and related methods are well known to one skilled in the art, and such methods and procedures have been described, for example, in standard references such as *Fiesers' Reagents for Organic Synthesis*, John Wiley and Sons, New York, NY, 2002; *Organic Reactions*, vols. 1-83, John Wiley and Sons, New York, NY, 2006; March J. and Smith M.: *Advanced Organic Chemistry*, 6th ed., John Wiley and Sons, New York, NY; and Larock R. C.: *Comprehensive Organic Transformations*, Wiley-VCH Publishers, New York, 1999.

Accordingly, the invention additionally provides a process for the preparation of the compound of formula S-(1), which comprises separation of the S-(1) isomer from a mixture with the R-(1) isomer by chromatography. The invention additionally provides a process for the preparation of the compound of formula S-(1), which comprises separation of the S-(1) isomer from a mixture with the R-(1) isomer and the compound of formula (2) by chromatography. Preferably, the compound of formula S-(1) is prepared by reaction of the compound of formula (13) with 3,3-dimethoxy-1-propene to give the acetal compound of formula (3) followed by isolation of the compound of formula S-(1) by chromatography. The chromatography is preferably conducted using silica gel as herein described.

An alternative method for synthesizing the compound of formula (1) is shown in Scheme 5.

Scheme 5

-continued

31

-continued (or 36b 2,6-dimethoxy isomer)

hydrolysis →

1

4 oxidation →

+ silylation → reduction →

32

-continued

Acetylation →

Deprotection →

Acetal
Formation →

Coupling →

OR or 36b 2,6-dimethoxy isomer

A preferred method for synthesizing the compound of formula (1) is shown in Scheme 6.

Scheme 6

-continued

Another preferred method for synthesizing the compound of formula (1) is detailed below with reference to Scheme 7.

Scheme 7

37

38

-continued

I. Oxidation of 10 DAB III, Formula (4):

A 4 L reaction flask, rinsed with dried EtOAc (300 mL) and held under $N_2$, was charged with dried EtOAc (1250 mL). Agitation was begun and dried (4) (100 g, 0.184 mol) was added. The addition of USP EtOH (800 mL) followed and the reaction mixture was cooled to −1.3° C. (internal temperature). Anhydrous $CuCl_2$ (86.4 g, 3.5 eq) was added and solids from the sides of the flask were washed into the mixture with anhydrous EtOH (450 mL). The reaction mixture was cooled to ≤−13° C. and anhydrous TEA (90 mL, 3.5 eq) was added slowly. The reaction was monitored by HPLC/TLC. At 1 h the reaction was judged complete (<5% (4)).

TFA (36 mL) was added to quench the reaction and stirring continued for 15 min. The reaction mixture was transferred to a 10 L rotovap flask. EtOAc (500 mL) and EtOH (300 mL) were added to the reaction flask, stirred for 2 min and the rinse added to the contents of the rotovap flask, which was evaporated on the rotovap at 40° C. until no further distillation occurred (80 min). Acidified ethanol (300 mL) was added to the residue and the resulting slurry was transferred to a 2 L rotovap flask. The first rotovap flask was rinsed into the second with acidified EtOH (400 mL). Again, the mixture was evaporated on the rotovap at 40° C. until no further distillation occurred (1 h). Acidified ethanol (305 mL) was added to the rotovap flask and the mixture was stirred on the rotovap at 40° C. for 10 min. The contents of the flask were then cooled to 5° C. and filtered. The rotovap flask was rinsed (2×) with cold (2° C.) acidified ethanol (300 mL) and the rinse was transferred completely to the filter to wash the solids. The solids were dried in the vacuum oven overnight at 45° C. to give (29a). HPLC Area %=91.3%. Yield=96.72 g.

II. Tesylation of (29a) to Form (30):

To (29a) (96.72 g, 0.1783 mmol) in a 10 L rotovap flask was added ethyl acetate (3000 mL, 30 mL/g). The solution was evaporated on the rotovap at 40° C. to approximately half the original volume (distilled volume=1680 mL). Toluene (1000 mL, 10 mL/g) was added to the remaining solution and it was evaporated on the rotovap at 40° C. until solids were obtained (45 min). The solids were suspended in toluene (1000 mL, 10 mL/g) and the suspension was evaporated on the rotovap at 40° C. (~1 h) to dry solids. The solids were transferred to a 2 L flask equipped with a mechanical stirrer, thermocouple, addition funnel and $N_2$ stream (previously purged for 5 min). The solids in the rotovap flask were rinsed into the reaction flask with anhydrous pyridine (292 mL, 3 mL/g) and agitation was begun. Upon dissolution, agitation was continued and the contents of the flask were cooled to −20° C. Triethylsilyl trifluoromethanesulfonate (120.9 mL, 3.0 eq) was slowly added to the reaction mixture to maintain the internal temperature of the reaction at ≤−10° C. After the addition of TES-OTf was complete, the reaction mixture was allowed to warm to −5.8° C. and agitation continued. Thirty minutes after the addition of TES-OTf, sampling was begun and continued at thirty-minute intervals for HPLC/TLC. The reaction was judged complete at 2 h when HPLC/TLC indicated <2% mono-TES derivative remaining.

The reaction mixture was cooled to −17.5° C. Methanol (19.3 mL, 0.2 mL/g) was added to quench the reaction and the reaction mixture was stirred for 5 min. While allowing the mixture to warm to ambient temperature, MTBE (500 mL) was slowly added with stirring and the mixture was transferred to a separatory funnel. Residues remaining in the reaction flask were washed into the separatory funnel with additional MTBE (200 mL, 2 mL/g), then water (250 mL, 2.5 mL/g) and saturated $NH_4Cl$ solution (250 mL, 2.5 mL/g) were added. The mixture was agitated and the layers were separated. The organic layer was transferred to a clean container. MTBE (250 mL, 2 mL/g) was added to the aqueous layer. It was agitated and the layers were separated. The second organic layer was washed into the first organic layer with MTBE (100 mL) and water (200 mL, 2 mL/g) was added to the combined layers. This mixture was agitated and the layers were separated. The organic layer was transferred to a 2 L rotovap flask and evaporated to a residue at 40° C. n-Heptane (500 mL, 5 mL/g) was added to this residue and the solution was again evaporated to a residue at 40° C. n-Heptane (1000 mL, ~10 mL/g) was added again and the solution was evaporated to one-half of its volume (distilled volume=375 mL). n-Heptane (300 mL, ~2.5 mL/g) was added and the solution was stirred for 35 min on the rotovap at 40° C. The solution was then cooled to −15.7° C. while stirring was continued for ~2.5 h. The solution was filtered. The solids remaining in the flask were rinsed into the filtration funnel with cold (<5° C.) n-heptane (100 mL) and all the solids were collected and dried overnight in the vacuum oven to give 111.2 g (30). HPLC Area % purity=93.4%.

III. Reduction of (30) to Prepare (31):

To a stirred solution of THF (560 mL, 5 mL/g) under $N_2$ in a 4 L reaction flask, was added (30) (111 g, 0.144 mol) followed by anhydrous ethanol (560 mL, 5 mL/g). The mixture was stirred to dissolve the solids and then cooled to −12° C. 2 M $LiBH_4$ in THF (72 mL) was added slowly to control the reaction temperature (temp=−11.9 to −9.7° C.). The reaction mixture was stirred and sampled for HPLC/TLC at 30 min intervals. Additional 2 M $LiBH_4$ in THF was introduced slowly (72 mL, 1.0 eq) to the reaction flask (temp=−9.6° C. to −7.1° C.) and agitation continued for 30 min. A third addition of 2 M $LiBH_4$ in THF (36 mL, 0.5 eq) was made in the same manner as the previous additions (temp=−7.6° C. to −6.7° C.), but with the bath temperature adjusted to 15° C. following the addition of the $LiBH_4$ solution and to 12.5° C. ten minutes later. At 1 h following the final $LiBH_4$ addition, the reaction was judged complete (mono reduced product ≤3% relative to (31)).

The reaction mixture was cooled to −10.8° C. and 10% ammonium acetate in EtOH (560 mL) was added slowly and cautiously to allow the foam to settle and to control the temperature of the solution ≤−3° C. The reaction mixture was transferred to a 2 L rotovap flask and any residues in the reaction flask were rinsed into the rotovap flask with EtOH (250 mL) and the contents of the rotovap flask were evaporated on the rotovap at 40° C. to an oil. Methanol (560 mL) was added to the residue. Water (1700 mL) was added to a 5 L flask equipped with an addition funnel and mechanical stirrer and was vigorously agitated. To precipitate the product, the methanol solution of the reaction mixture (748 mL) was slowly added to the flask containing water. The resulting mixture was filtered and the solids were washed with water (650 mL). A portion of the water was used to wash solids remaining in the precipitation flask into the filtration funnel. The solids were placed in the vacuum oven overnight at 45° C. to give 139.5 g of slightly wet non-homogeneous product, (31). HPLC area % purity=92.8%.

IV. Acetylation/Deprotection of (31) to Prepare (33):

Acetylation: To (31) (138 g, 0.178 mol) in a 2 L rotovap flask was added IPAc (1400 mL, 10 mL/g). The solution was evaporated on the rotovap at 40° C. to an oil. The procedure was repeated. Dried IPAc (550 mL) was then added to the residual oil and the contents of the rotovap flask were transferred to a 1 L reaction flask, equipped with a mechanical stirrer, addition funnel, thermocouple and a $N_2$ stream. The rotovap flask was washed into the reaction flask with IPAc (140 mL). DMAP (8.72 g, 0.4 eq), anhydrous TEA (170 mL, 7 eq) and acetic anhydride (100.6 mL, 6 eq) were added to the contents of the reaction flask and the mixture was stirred and heated to 35° C. While continuing agitation and heating to 35° C., the reaction was monitored by HPLC/TLC at 1-hour intervals.

Upon completion of the reaction, as indicated by the absence of (31) (3 h total time), the reaction mixture was cooled to 19.7° C. and saturated ammonium chloride solution (552 mL) was added. After stirring for 15 min, the mixture was transferred to a separatory funnel, the layers were separated and the aqueous layer was removed. Water (280 mL) was added to the organic layer and the mixture was stirred for 4 min. The layers were again separated and the aqueous layer was removed. The organic layer was transferred to a 2 L rotovap flask and the remaining content of the separatory funnel was washed into the rotovap flask with IPAc (200 mL). The mixture was evaporated to dryness on the rotovap at 40° C. to give ~124 g (32) as pale yellow oily foam.

Deprotection: To the rotovap flask containing (32) (124 g) was added methanol (970 mL, 7 mL/g). Sampling for HPLC/TLC was begun and continued at 1-hour intervals. The (32)/methanol solution was transferred to a 3 L reaction flask and agitation was begun. The remaining content of the rotovap flask was washed into the reaction flask with methanol (400 mL). Acetic acid (410 mL, 3 mL/g) and water (275 mL, 2 mL/g) were added and the reaction mixture was heated to 50° C. and stirred. With the temperature maintained between 50° C. and 55° C., the reaction was monitored by HPLC/TLC at 1-hour intervals for the disappearance of the starting material, formation and disappearance of the mono-TES intermediate and formation of the product, (33).

Upon completion (~9 h), the reaction mixture was cooled to rt and transferred to a 10 L rotovap flask. Solvent exchanges to n-heptane (2×1370 mL, 1×1000 mL) and IPAc (2×1370 mL, 1×1500 mL) were performed. IPAc (280 mL, 2 mL/g) and silica (140 g, 1 g/g) were added to the rotovap flask and the contents were evaporated on the rotovap at 40° C. until no further distillation occurred and free flowing solids were obtained. The dry silica mixture was loaded onto a silica pad (7 cm column, 280 g silica), conditioned with 2:1 n-heptane/IPAc (500 mL, 2 mL/g silica) and washed (4×) with 2:1 n-heptane/IPAc, 2 mL/g silica, 3400 mL total) and (4×) with 1:1 n-heptane/IPAc (3020 mL total, 2 mL/g silica) until all impurities were removed as indicated by TLC. Each wash (~840 mL) was collected as a separate fraction and analyzed by TLC. The silica pad was then washed (5×) with waEtOAc (1% water, 1% AcOH in EtOAc) (3950 mL total, 2 mL/g silica) and with 1:1 MeOH/EtOAc and each wash (~840 mL) was collected as a separate fraction. The product eluted with fractions 11-15. The fractions containing (33) as indicated by HPLC/TLC were combined, transferred to a rotovap flask and evaporated to dryness on the rotovap at 40° C. The residue in the flask was dissolved and evaporated to dryness: first with IPAc (1055 mL) and n-heptane (550 mL) and a second time with IPAc (830 mL) and n-heptane (410 mL). IPAc (500 mL) was then added to the residue, the solution was transferred to a 2 L round bottom flask and n-heptane (140 mL) was added. The resulting solution was evaporated on the rotovap and dried in the vacuum oven at 40° C. to give (33) as foam. To dissolve the foam, IPAc (160 mL) was added to the flask followed by toluene (800 mL). The solution was evaporated on the rotovap under vacuum at 50° C. until half of the solvent was removed and solids were forming. The contents of the flask were stirred and cooled to 21° C. for 1.5 h. The solids were filtered in a 90 cm filtration funnel on #54 Whatman filter paper and were washed with toluene (165 mL), transferred to the vacuum oven and dried at 40° C. to give 62.6 g of (33). HPLC area %=96.9%

VI. Acetal Formation: (33) to (34)

To a 3 L reaction flask containing (33) (25 g, 42.4 mmol) was added toluene (375 mL) and the reaction mixture was cooled to ~−15° C. TFA (9.8 mL, 3.0 eq) was slowly added. This was followed by the addition of acrolein diethyl acetal (8.7 g) and the reaction was monitored by HPLC until <3% of (33) remained.

Hydrated silica was prepared by mixing silica (25 g) and water (25%) and a "basified silica" mixture was prepared by mixing a solution of $K_2CO_3$ (17.6 g, 3.0 eq) in water (1 mL/g (33)) with 50 g silica. Upon reaction completion, the hydrated silica was added to the reaction mixture and it was stirred for 30 to 45 min while maintaining the temperature ≤5° C. The basified silica was then added to the mixture while continuing to maintain the temperature ≤5° C. and the pH>5. After stirring for ~15 min, the mixture was filtered. The silica was washed with ~20 mL/g toluene and the filtrates were combined and concentrated. The residue was digested with 1 mL/g toluene for ~4 h. The resultant solids were filtered and washed with 80:20 toluene/heptane to give 25 g of (34). HPLC area %=98%. Mass yield=66%.

VII. Preparation of Compound (1) from (34):

To THF (300 mL, 8 mL/g) stirring in a 1 L reaction flask (rinsed with THF (500 mL)) was added (34) (35.7 g, 0.0570 mol). Purified (35a) (30.9 g, 1.25 eq) was added to the reaction mixture followed by the addition of NMM (11.5 mL, 1.8 eq), DMAP (2.77 g, 0.4 eq) and THF (75 mL, 2 mL/g). The mixture was stirred while $N_2$ was bubbled from the bottom of the flask to mix and dissolve the solids. Pivaloyl chloride (11.5 mL, 1.6 eq) was then added slowly to the reaction mixture. The reaction mixture was warmed and the temperature maintained at 38° C.±4° C. while stirring continued and $N_2$ continued to be bubbled from the bottom of the flask. The reaction mixture was analyzed by HPLC/TLC for consumption of starting material and formation of the coupled ester, (36a), at 30 min intervals beginning 30 min after the addition of the pivaloyl chloride.

After 1 h the reaction was judged complete and the reaction mixture was cooled to 2° C. 0.5 N HCl in MeOH (280 mL, ~20 mL/mL NMM) was added to maintain the pH of the reaction mixture=1.5-1.9. The reaction mixture was stirred at 2° C.±2° C. and monitored by HPLC/TLC at 30 min intervals for consumption of (36a) and formation of (1) and the acrolein acetal hydrolyzed by-product. Upon completion at 2 h the reaction was quenched with 5% aqueous sodium bicarbonate (300 mL) and IPAc (185 mL, 5 mL/g) was added. The reaction mixture was transferred to a 2 L rotovap flask and the reaction flask rinsed into the rotovap flask 2× with 60 mL IPAc. The mixture was evaporated under vacuum at 40° C. until a mixture of oil and water was obtained. IPAc (200 mL) was added to the oil and water mixture and the contents of the flask were transferred to a separatory funnel. The reaction flask was rinsed into the separatory funnel with IPAc (100 mL) and the contents of the separatory funnel were agitated and the layers were separated. The aqueous layer was removed. Water (70 mL) was added to the organic layer and, after agitation, the layers were separated and the aqueous layer was removed. The organic layer was transferred to a rotovap flask and evaporated under vacuum at 40° C. to a foam, which was dried in the vacuum oven to give 64.8 g crude (1). HPLC area %=45.5%.

VIII. Purification Procedures:

Normal Phase Chromatography: The 6″ Varian DAC column was packed with Kromasil (5 Kg, 10 µm, 100 Å normal phase silica gel). The 50-cm bed length provided a 9 L empty column volume (eCV). The column had been regenerated (1 eCV 80:20 waMTBE:MeOH) and re-equilibrated (1 eCV waMTBE, 1 eCV 65:35 n-heptane:waMTBE).

The crude (1) (64.70 g), was dissolved in MTBE (180 mL) and heated to ~40° C. n-Heptane (280 mL) was slowly added to the solution. This load solution was pumped onto the column using a FMI "Q" pump. The column was then eluted with 65:35 n-heptane:waMTBE at 800 mL/min. A 34 L forerun (~3.8 eCV) was collected followed by 24 fractions (500 mL each). Fractions 1 through 23 were combined and concentrated to dryness on a rotovapor. The residue was dried in the vacuum oven overnight to provide 41.74 g (1). HPLC area %=99.4%.

Final Purification: The normal phase pool was dissolved in USP EtOH (6 mL/g) and concentrated to dryness three times. The resultant residue was dissolved in USP EtOH (2 mL/g). This ethanolic solution was slowly added drop-wise to water (deionized, 20 mL/g) with vigorous stirring. The resultant solids were vacuum filtered and washed with cold DI water. The solids were dried in the vacuum oven at 40° C. overnight to give 38.85 g (1). HPLC area %=99.5%.

IX. Coupling of (35b) to (34) to Form (1):

Anhydride/Coupling (35b) with (34): A 10 mL round bottom flask with two necks was heated to eliminate water, then allowed to cool under N$_2$ atmosphere. To the flask was added (34) (125 mg, 0.2 mmol), THF (1.25 mL), 4-methylmorpholine (40 µL, 0.36 mmol), DMAP (10.9 mg, 0.009 mmol), (35b) sodium salt (110 mg, 0.254 mmol) and finally trimethylacetyl chloride (40 µL, 0.319 mmol). The reaction mixture was stirred at 40° C. under N$_2$. After about 2 hours, additional 4-methylmorpholine (11 µL, 0.01 mmol), (35b) sodium salt (41 mg, 0.1 mmol) and trimethylacetyl chloride (13 µL, 0.1 mmol) were added to assist formation of the anhydride intermediate which then coupled to (34). After about 2 additional hours, 4-methylmorpholine (11 µL, 0.010 mmol), trimethylacetyl chloride (13 µL, 0.104 mmol) and (35b) sodium salt (42 mg, 0.1 mmol) were added. After 1.5 hours more, the reaction was placed into a freezer at −20° C. overnight. The following morning, stirring was resumed and the reaction was heated to 45° C. for 2 hours. Additional 4-methylmorpholine (22 µL, 0.02 mmol) and trimethylacetyl chloride (25 µL, 0.201 mmol) were added. An additional 2 hours of stirring resulted in the reaction reaching ~90% completion.

To quench, the reaction mixture was removed from heat and allowed to cool to RT with stirring, and MTBE (2 mL) was added followed by water (1 mL). The mixture was partitioned and the organic phase was washed with brine (40 µL). The organic phase was concentrated at 40° C. to obtain crude product as a pink foam. The pink foam was dissolved into MTBE (500 µL) and added dropwise to stirring n-heptane (5 mL) at ~−20° C. to give pink precipitate. The mixture was vacuum filtered and the solids were dried overnight in a vacuum oven at 40° C. to yield the desired coupled ester (82 mg), as indicated by LC/MS. The coupled ester (36b) was purified by flash chromatography on normal phase silica, eluting with an IPAc/n-heptane system of increasing polarity. Approximately 26 mg of the purified coupled ester (36b) was recovered as confirmed by LC/MS.

Deprotection of (36b) to Form (1):

The coupled ester (36b) (15 mg, 0.001 mmol) was dissolved into THF (1 mL). A 250 µL aliquot of the solution was diluted 1:1 with THF. The solution was stirred on an ice bath at ~0° C., after which HCl (0.5 N in MeOH, 25 µL) was added. The reaction was monitored by LC/MS, which indicated the formation of (1).

Methods for the preparation of the compounds of formula 35a and 35b and further suitable coupling conditions for converting the compound of formula (34) into the compound of formula (1) are described in WO 2007/126893.

Chemical Example 1. Separation of Diastereoisomers of Formula (3) by Normal Phase Chromatography A solution of the compound of formula (3), which comprises a mixture of diasteroisomers of formula (1) and formula (2) (570 mg) was concentrated to light yellow oil, dried in the vacuum oven for 15 min and re-dissolved in 35:65 MTBE/n-heptane. The solution was loaded onto a flash chromatography column packed with spherical silica (YMC-1701, 56 g), which had been conditioned with 35:65 MTBE/n-heptane. The solution flask was rinsed (2×) with ~2 mL of MTBE onto the column. The column was eluted with 35:65 MTBE/n-heptane and fractions (25 mL) were collected. Fractions containing the pure product (fractions 23-25) as indicated by visual spotting (to identify the elution of UV active material) and by TLC analysis (50:50 MTBE/n-heptane) were collected, pooled and concentrated to give 305 mg of the diastereoisomer of formula S-(1) as a white solid.

The compound S-(1) was characterized by NMR, including $^1$H, $^{13}$C, HMBC, HSQC, NOESY, COSY and gHSQMBC. The compound of formula S-(1) was also analyzed by β-tubulin binding modeling studies. Similarly compound R-(1) was also characterized by NMR, including $^1$H, $^{13}$C, HMBC, HSQC, NOESY, COSY and gHSQMBC.

Additionally, the invention additionally provides a process for the preparation of the compound of formula S-(34), which comprises separation of the S-(34) isomer from a mixture with the R-(34) isomer by chromatography.

Properties and Uses of the Compounds of the Invention

The present application provides various methods of treating abnormal cell growth in a mammal, such as a human, by administering to the mammal a therapeutically effective amount of a composition comprising the compound of formula S-(1) or pharmaceutically acceptable salts, solvates or hydrates thereof.

In one aspect of the above method, the composition comprising the compound of formula S-(1) is administered via parenteral administration. In another aspect of the above method, the parenteral administration is via intravenous injection or infusion. In another aspect of the above method, the parenteral administration is for about 60 minutes or less. In another aspect of the above methods, the administration of the intravenous infusion is once every 7 days for 3 weeks, followed by a 7 day rest period, in a 28 day cycle, for at least one cycle. In one particular variation of the above methods, the administration of the intravenous infusion is once every 21 days, in a 21 day cycle, for at least one cycle.

In one aspect of the methods above, the intravenous infusion comprises the compound of formula S-(1) at a dose of 240 mg/m$^2$ or less, or 185 mg/m$^2$ or less. In another aspect of the methods above, the intravenous infusion comprises the compound of formula S-(1) at a dose of 185 mg/m$^2$ or less, or 160 mg/m$^2$ or less. Such amounts can often be reflected in unit doses of about 200 mg to 400 mg, for example about 250 mg, 300 mg or 350 mg.

In one aspect of any of the above-mentioned embodiments of the invention, the composition comprising the compound of formula S-(1) comprises a polyethoxylated castor oil formulation.

Preferably, the polyethoxylated castor oil formulation is about 50% ethanol and about 50% polyethoxylated castor oil or about 85% ethanol and about 15% polyethoxylated castor oil.

In one embodiment of the application, the composition comprising the compound of formula S-(1) may be administered parenterally, orally, subcutaneously, or intraperitoneally. In another embodiment of any of the above-mentioned embodiments of the invention, the composition comprising the compound of formula S-(1) further comprises one or more pharmaceutically acceptable, inert or physiologically active excipients, diluents or adjuvants selected from the group consisting of phomopsin, dolastatin, bevacizumab (Avastin™), steganacin, paclitaxel, taxotere, vinblastine, vincristine, vindesine, vinorelbine, navelbine, colchicine, maytansine, ansamitocin, Iressa, Tarceva, Herceptin, lapatinib, vandetanib, Sorafenib, BAY-57-9006, bevacizumab, cetuximab, gemtuzumab, panitumumab, rituximab, tositumomab, trastuzumab, apolizumab, oregovomab, mitumomab, alembuzumab, ibritumomab, vitaxin, SU-6668, semaxanib, sunitinib malate, SU-14813, vandetanib, Recentin, CP-547632, CEP-7055, AG-013736, pazopanib, combretastatin, squalamine, combrestatin A4 phosphate, TNP-470, neovastat, dasatinib, imatinib, nilotinib, sorafenib, sunitinib, triethylenethiophosphoramine, alitretinoin, altretamine, arsenic trioxide, asparaginase, bexarotene, denileukin diftitox, hydroxycarbamide, masoprocol, mitotane, pegaspargase, tretinoin, raltitrexed, IL-10, IL-12, bortezomib, leuprolide, interferon □, pegylated interferons, atrasentan, melphalan, cyclophosphamide, chlormethine, chlorambucil, trofosfamide, ifosfamide, nitromin, busulfan, thiotepa, chlorambucil, CC-1065, temozolomide, pipobroman, dacarbazine, mechlorethamine, procarbazine, uramustine, RSU-1069, CB-1954, hexamethylmelamine, cisplatin, carboplatin, oxaliplatin, BBR3464, satraplatin, tetraplatin, iproplatin, amsacrine, netropsin, pibenzimol, mitomycin, duocarmycin, dactinomycin, distamycin, mithramycin, chromomycin, olivomycin, anthramycin, bleomycin, liblomycin, rifamycin, actinomycin, adramycin, trichostatin A, propamidine, stilbamidine, rhizoxin, nitroacridine, geldamycin, 17-AAG, 17-DMAG, plicamycin, deoxycoformycin, levamisole, daunorubicin, doxorubicin, epirubicin, idarubicin, mitroxantrone, valrubicin, carmustine, fotemustine, lomustine, streptozocin, gemcitabine, 5-fluorouracil (5-FU), fludarabine, cytarabine, capecitabine, mercaptopurine, cladribine, clofarabine, thioguanine, pentostatin, floxuridine, pentostatin, aminopterin, methotrexate, pemetrexed, camptothecin, irinotecan, topotecan, epipodophyllotoxin, etoposide, teniposide, aminogluthetimide, anastrozole, exemestane formestane, letrozole, fadrozole, aminoglutethimide, leuprorelin, buserelin, goserelin, triptorelin, abarelix, estramustine, megestrol, flutamide, casodex, anandron, cyproterone acetate, finasteride, bicalutamide, tamoxifen or its citrate salt, droloxifene, trioxifene, raloxifene or zindoxifene, a derivative of 17-β-estradiol such as ICI 164, ICI 384, ICI 182, ICI 780, testolactone, fulvestrant, toremifene, testosterone, fluoxymesterone, dexamethasone, triamcinolone, dromostanolone propionate, megestrol acetate, methyltestosterone, chlorotrianisene, hydroxyprogesterone, medroxyprogesterone acetate, reloxafine, etanercept, thalidomide, revimid (CC-5013), aziridoquinones, misonidazole, NLA-1, RB-6145, misonidazole, nimorazole, RSU-1069, SR-4233, porfimer, photofrin, verteporfin, merocyanin 540, tin etiopurpurin, PUVA, aminolevulinic acid, methyl aminolevulinate, minodronate, zoledronic acid, ibandronate sodium hydrate or clodronate disodium, misonidazole, misonidazole, amifostene, oblimersen, TIMP-1 or TIMP-2, marimastat, TLK-286 and mixtures thereof.

In a preferred embodiment, the one or more pharmaceutically acceptable adjuvants is temozolomide. In another preferred embodiment, the one or more pharmaceutically acceptable adjuvants is bevacizumab (Avastin™).

The compound of the invention may be useful in the treatment of diseases when used alone or in combination with other therapies. For example, when used for the treatment of cancer, the compounds of the invention may be administered alone or in combination with radiotherapy, surgical removal, hormonal agents, antibodies, antiangiogenics, COX-2 inhibitors, and/or other chemotherapeutic agents such as taxanes, temozolomide, cisplatin, 5-fluorouracil, taxotere, gemcitabine, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

The compound of the invention may be useful in the treatment of diseases when used alone or in combination with other chemotherapeutics. For example, when used for the treatment of cancer, the compounds of the invention may be administered alone or in combination with aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platin containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, aminopeptidase inhibitors, thymidilate synthase inhibitors, a DNA cross linking agents, topoisomerase I or II inhibitors, DNA alkylating agents, ribonuclease reductase inhibitors, cytotoxic factors, and growth factor inhibitors.

In one aspect of the invention the composition comprising the compound of formula S-(1) further comprises one or more pharmaceutically acceptable, inert or physiologically active diluents or adjuvants selected from the group consisting of cytostatic agent, cytotoxic agent, taxane, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

In another aspect of the invention, the composition comprising the compound of formula S-(1) may be administered alone or in combination with one or more anti-cancer therapies. In another aspect of the invention, the one or more anti-cancer therapies is a chemotherapeutic agent. In another aspect of the invention, the one or more anti-cancer therapies is radiation therapy.

In another embodiment of the invention, the one or more anti-cancer therapies is surgical removal of a tumor. In one aspect of the above-mentioned embodiments of the invention, the composition comprising the compound of formula S-(1) may be administered as a single infusion once every 21 days in a 21 day cycle. In another aspect of the invention, the composition comprising the compound of formula S-(1) may be administered as a single infusion once every seven days, followed by a rest week, in a 28 day cycle. Dose levels on this schedule may exceed 185 mg/m$^2$ per infusion, with chemo-naive patients tolerating greater dosing levels, but even in heavily pretreated patients, dosing of 126 mg/m$^2$ or 150 mg/m$^2$ is well tolerated.

In one embodiment of the invention, the composition comprising the compound of formula S-(1) may be administered before the one or more chemotherapeutic agents. In one aspect of the invention, the composition comprising the compound of formula S-(1) may be administered after the one or more chemotherapeutic agents. In another aspect, the composition comprising the compound of formula S-(1) may be administered before the radiation therapy. In yet another aspect, the composition comprising the compound of formula S-(1) may be administered after the radiation therapy.

In one particular aspect of the above-mentioned embodiments of the invention, the composition comprising the compound of formula S-(1) may be administered before the surgical removal. In another aspect, the composition comprising the compound of formula S-(1) may be administered after the surgical removal.

The application also provides compositions for and a method of potentiating the therapeutic benefit of a multi-drug chemotherapeutic regimen, wherein one of the drugs in the regimen comprises the compound of formula S-(1), by administering the compound of formula S-(1) as an intravenous formulation. In one embodiment of the invention, the intravenous formulation comprises the compound of formula S-(1) given at a high dose.

In another embodiment of the invention, an additional drug in the regimen comprises an anti-mitotic agent or anti-microtubule agent. In one variation, the dose of a single infusion of the compound of formula S-(1) exceeds 160 mg/m$^2$. In another variation, the dose of a single infusion of the compound of formula S-(1) exceeds 185 mg/m$^2$.

The application also provides compositions for and a method to produce prolonged elevated plasma levels of the compound of formula S-(1) to promote synergistic interaction between the compound of formula S-(1) and a one or more other chemotherapeutic agents, wherein: the compound of formula S-(1) is administered as an intravenous formulation, and the compound of formula S-(1) is administered on the day of, or within 3 days of administration of the one or more other chemotherapeutic agents. In one aspect of the invention, the one or more other chemotherapeutic agents comprises an anti-mitotic agent or anti-microtubule agent. In another aspect of the invention, the intravenous formulation comprises temozolomide and/or bevacizumab (Avastin™).

The application also provides compositions for and a method of binding microtubules in cancer cells comprising contacting the cells with an effective amount of the compound of formula S-(1). The application also provides compositions for and a method of hindering or preventing mitosis in cancer cells comprising contacting the cells with an effective amount of the compound of formula S-(1). In one aspect of the invention, the cancer cells are pancreatic, breast, or colorectal cancer cells.

The application also provides compositions for and a method of assaying for cancer cell sensitivity to the compound of formula S-(1) comprising: a) providing a cancer cell; b) contacting the cancer cell with a composition comprising the compound of formula S-(1); c) analyzing the cancer cell for inhibition of growth; and d) comparing the inhibition of growth in the cancer cell from step (c) with the inhibition of growth in the cancer cell in the absence of the compound of formula S-(1), wherein growth inhibition by the compound of formula S-(1) indicates that the cancer cell is susceptible to the compound of formula S-(1).

In one embodiment of the invention, the method further comprises assaying for mitotic arrest in a cancer cell.

BRIEF DESCRIPTION OF THE FIGURES

FIGS. 4A, 4B, and 4C. S-(1) Oral efficacy in Mice.

FIGS. 9A and 9B. Efficacy Comparison in Prostate Tumor Xenograft Model.

Figure 1:
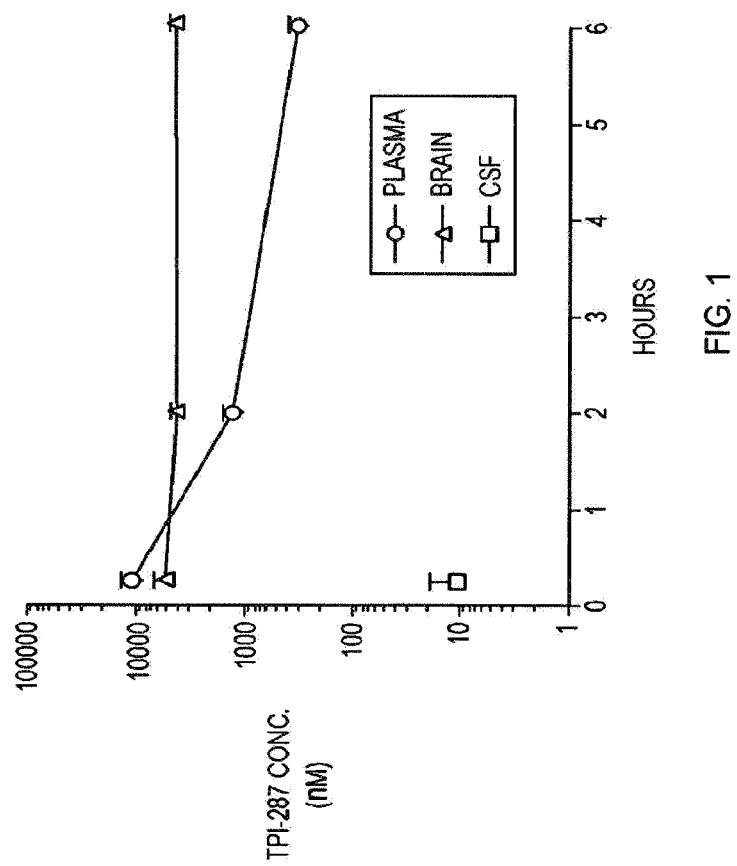
FIG. 1. S-(1) crosses rat blood-brain barrier.

The compound of formula S-(1) may be administered by any conventional route of administration including, but not limited to, oral, pulmonary, intraperitoneal (ip), intravenous (iv), intramuscular (im), subcutaneous (sc), transdermal, buccal, nasal, sublingual, ocular, rectal and vaginal. It will be readily apparent to those skilled in the art that any dosage or frequency of administration that provides the desired therapeutic effect is suitable for use in the present application.

The therapeutically effective amount of the compound of formula S-(1) may be administered by week or by 21 days for a total dose of about 7-555 mg/m$^2$, or 7-240 mg/m$^2$, or 7-185 mg/m$^2$ during a 21 day period. The dosages, however, may be varied depending on the requirements of the subject to be treated, including sex, age, weight, diet, etc. The precise amount of the compound of formula S-(1) required to be administered depends on the judgment of the practitioner and is peculiar to each individual.

Another embodiment of the present application is a pharmaceutical composition for treating brain tumor, comprising a therapeutically effective amount of the compound of formula S-(1) and a pharmaceutically acceptable carrier.

Another embodiment of the present application is a pharmaceutical composition for oral administration of the compound being patient friendly. The solubility properties of the compound of formula S-(1) are such that high concentration of the compound of formula S-(1) can be achieved in pharmaceutically acceptable carriers, between 75 and 200 mg/ml, that can be filled in hard and soft gelatin capsules with an appropriate chemical and physical stability profile.

To prepare a pharmaceutical composition of the present application, the compound of formula S-(1) is admixed with a pharmaceutically acceptable carrier according to conventional pharmaceutical compounding techniques, wherein the carrier may take a wide variety of forms depending on the form of preparation desired for administration. Suitable pharmaceutically acceptable carriers are well known in the art. Descriptions of some pharmaceutically acceptable carriers may be found in The Handbook of Pharmaceutical Excipients Eds. Rowe et al., American Pharmaceutical Association and the Pharmaceutical Society of Great Britain.

The pharmaceutical composition of the present application may be, depending on the route of administration, in the form of a tablet, pill, capsule, granule, powder, ointment, gel, solution, sterile parenteral solution or suspension, metered aerosol or liquid spray, or suppository that may contain micro or nano particles, a colloid, liposome or a biocompatible or biodegradable medium.

As a solid dosage form, the pharmaceutical composition of the present application may comprise, in addition to the compound of formula S-(1), at least one diluent, binder, adhesive, disintegrant, lubricant, antiadherent, and/or glidant. Additionally, sweeteners, flavorants, colorants and/or coatings may be added for specific purposes.

As a liquid dosage form, the pharmaceutical composition of the present application may comprise, in addition to the compound of formula S-(1) and a liquid vehicle, at least one wetting agent, dispersant, flocculation agent, thickener, buffer, emulsifier, amphiphilic, osmotic agent, coloring agent, anti-oxidant, flavor, fragrance, and/or preservative.

Such a possible liquid formulation includes a sterile solution containing 10 mg/mL of the compound of formula S-(1) in a 15:85 or 50:50 (w/v) polyoxyl 35 castor oil/ dehydrated alcohol solution. An appropriate pharmaceutical grade polyoxyl 35 castor oil is Cremophor EL-P, which is a non-ionic solubilizer made by reacting castor oil with ethylene oxide in a molar ratio of 1:35, followed by a purification process (BASF Pharma).

Other suitable agents for inclusion in such formulations are as described in WO 99/45918. Such additional carriers include vitamin E TPGS, oleic acid, Tweens such as Tween 80, lipid carriers used for parenteral nutrition, solutrol and the like. As shown in Table 10 below, these agents and the composition of the final formulation might have an impact of the pharmacokinetics of the compound and its pharmacodymanics and thus its tissue distribution.

As previously mentioned, the compound of the invention surprisingly may be administered orally as further exemplified below. Oral administration may involve swallowing, so that the compound enters the gastrointestinal tract, or buccal or sublingual administration may be employed by which the compound enters the blood stream directly from the mouth.

The therapeutically effective amount of the compound of formula S-(1) may be administered by the parenteral route using a weekly or 21 days schedule for a total dose of about 7-555 mg/m$^2$, or 7-240 mg/m$^2$, or 7-185 mg/m$^2$ during a 21 day period. The dosages, however, may be varied depending on the requirements of the subject to be treated, including sex, age, weight, diet, etc. The precise amount of the compound of formula S-(1) required to be administered depends on the judgment of the practitioner and is peculiar to each individual.

The compound of formula S-(1) may be administered by the oral route using a daily, weekly or 21 days schedule, and any schedule comprised within this range, for a total dose of about 5-600 mg/m$^2$, or 25-400 mg/m$^2$. The dosages, however, may be varied depending on the requirements of the subject to be treated, including sex, age, weight, diet, etc. The precise amount of the compound of formula S-(1) required to be administered depends on the judgment of the practitioner and is peculiar to each individual.

It is believed that the compounds and hence compositions of this invention possess an enhanced safety profile (for example, on the immune system or the blood) in comparison to marketed taxanes which offers the potential for enhanced or longer dosing schedules under the direction of the skilled physician than marketed taxanes.

The compositions may for oral administration contain at least 15 mg of the compound of the invention per dose, more aptly at least 50, 80, 100, 150, 200 mg and more aptly less than 250 mg per dose. However, the dosage may be varied as directed by the physician in view of the individual patient's response. A liquid composition will normally contain about 0.1 mg/ml to about 300 mg/ml for example about, 1, 5 10, 50, 100 or 150 mg/ml of the compound of the invention. A non-liquid composition may contain a proportion of the compound of the invention, for example 5% to 50%, such as 10, 20, 25 or 30% by weight. In the case of a liquid composition for parenteral administration, the composition will normally contain between 1 mg/ml and 50 mg/ml while the composition will normally contain between 40 mg/ml to 200 mg/ml if administered orally. WO 1999/ 45918 and the international patent applications and US patent applications referred to above discloses compositions that may be considered for use with compounds of the invention.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations. Liquid formulations include suspensions, solutions, syrups and elixirs. Such formulations may be employed as fillers in soft or hard capsules and typically comprise a carrier, for example, ethanol, polyethylene glycol, propylene glycol, methylcellulose, or a suitable oil, a lipohilic component with a high HLB value, an amphiphilic solvent, and one or more emulsifying agents and/or suspending agents. Liquid formulations may also be prepared by the reconstitution of a solid, for example, from a sachet. The compound of the invention may also be used in fast-dissolving, fast-disintegrating dosage forms. Tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methyl-cellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. Tablets may also generally contain lubricants such as magnesium stearate, calcium stearate, zinc stearate, sodium stearyl fumarate, and mixtures of magnesium stearate with sodium lauryl sulphate. Other possible ingredients include anti-oxidants, colourants, flavouring agents, preservatives and taste-masking agents. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

Consumable oral films are typically pliable water-soluble or water-swellable thin film dosage forms which may be rapidly dissolving or mucoadhesive and typically comprise the compound of formula S-(1), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, emulsifiers, salivary stimulating agents, cooling agents, co-solvents (including oils), emollients, bulking agents, anti-foaming agents, surfactants and taste-masking agents.

Solid formulations for oral administration may be formulated to be immediate and/or modified release. Modified release formulations include delayed-, sustained-, pulsed-, controlled-, targeted and programmed release.

BIOLOGICAL EXAMPLES

In Vitro $ED_{50}$ MT Polymerization Study

In this tubulin binding assay, microtubule protein (MTP) is used as a substrate. The assay contains bovine tubulin plus microtubule associated proteins (MAP). MTP is polymerized into microtubules in the presence of DAPI (4',6'-diamidino-2-phenylindole), a fluorescent compound. DAPI binds to tubulin; when microtubules are formed and there is an enhancement of fluorescence. The microtubule formation is measured as a function of time, using a fluorescence plate reader. The $ED_{50}$ values obtained with this method are in good agreement with older sedimentation techniques. The more current assay, using DAPI, is faster and uses less protein. The method used is based on the procedure published by Donna M. Barron, et al, "*Fluorescence-based high-throughput assay for antimicrotuble drugs*" Analytical Biochemistry, 315: 49-56, 2003, which is incorporated by reference in its entirety. The excitation wavelength, in that assay, was set at 370 nm and the emission wavelength was set at 450 nm for the DAPI experiments.

A Bio-Tek FL 600 microplate Fluorescence Reader was used to measure the relative level of fluorescence in the DAPI assay.

Assays were conducted in 96-well plates. Each well contained a total volume of 0.1 mL consisting of PEM buffer (0.1 M Pipes, 1 mM EGTA, 1 mM $MgCl_2$, pH 6.9), 0.2 mg bovine microtubule protein, and 10 µg of DAPI. Compounds having paclitaxel-like activity of varying concentrations dissolved in DMSO were added last. The final DMSO concentration was 4%. The plates were incubated at 37° C. for 30 minutes and read in a fluorescence plate reader using an excitation wavelength of 360 nm and an emission wavelength of 460 nm. Fluorescence values were corrected for the sample without compound. Results were expressed as a percent of maximum assembly, with maximum assembly taken to be that obtained at 25 µM paclitaxel.

Experiments were done twice in triplicate. Results were subsequently combined and fit to a non-linear regression program. The results from these studies summarized in Table 2 indicate that the S-(1) diastereoisomer has an $ED_{50}$ potency that is equal to or greater than that determined for other tubulin binding agents such as paclitaxel, docetaxel and Epothilone B.

TABLE 2

Summary of Tubulin Polymerization Assays, Comparison of S-(1) to paclitaxel, docetaxel, and epothilone B.

| Compound | ED50, µM | ED50 Compound/ED50 Paclitaxel |
|---|---|---|
| S-(1) | 1.58 ± 0.46 | 0.53 |
| Paclitaxel | 2.97 ± 0.50 | 1.00 |
| Docetaxel | 3.18 ± 0.45 | 1.07 |
| Epothilone B | 3.31 ± 0.51 | 1.11 |

MTS Proliferation Assay (Promega)

Day 1: Cells were plated in appropriate growth medium at $5 \times 10^3$ per well in 100 ul in 96 well tissue culture plates, Falcon, one for each drug to be tested. Col 1 was blank; it contained no cells, just medium. The plates were incubated overnight at 37° C., 5% $CO_2$ to allow attachment.

Day 2: Added 120 ul growth medium in wells of 96-well "dilution plates" (one for each drug) and let sit in 37° C. incubator for about 1 hr.

Thawed DMSO drug stocks (usually at 10 mM). Each drug was diluted 6 ul into a tube with 3 ml growth medium, to 20 µM.

Aspirated medium from col 12 of a dilution plate; added 200-300 ul of 20 uM drug to wells of col 12. Made serial dilution down this 96-well plate: for a 1:5 dilution pattern, moved 60 ul from col 12 to col 11, mixed 4-5 times (using 8 place multi-pipettor), moved 60 ul to col 10, etc. stopping at col 3.

Moved 100 ul of medium+drug from dilution plate to a cell plate, i.e. col 1 from drug plate (blank=no cells) to col 1 of cell plate, etc. up to col 12. Col 2 contained cells with no drug. Col 3 had the lowest concentration of drug (0.005 nM) and col 12 had the highest drug concentration (10 µM).

Day 4 or 5: Terminated the assay 48 to 72 hrs after drug addition. Thawed MTS reagent; made up enough medium+ MTS to cover all plates at 115 ul per well (100 ul medium+ 15 ul MTS). Aspirated medium+drugs from cell plate; replaced with medium+MTS mix and incubated 1-6 hrs (37° C., 5% $CO_2$), depending on cell type. When the color turned dark in control wells (col 2), and was still light in col 12, the absorbance at 490 nm was read on a plate reader; the results were used to calculate $IC_{50}$.

The effects of the compound of formula S-(1) measured in in vitro and xenograft animal models of various brain cancers were evaluated in the following experimental examples, which are intended to be a way of illustrating but not limiting the present application.

S-(1) Pharmacokinetic Data in Mouse Model:

S-(1) was formulated in 7% Ethanol: 3% Cremophor EL: 90% D5W (5% Dextrose in water). The formulated drug was administered as a single IV bolus via tail vein injection. The details are set out below:

Animal Information:

| Species | Strain | Sex | Wt. Range (g) | Total No. Required | Source | Fasted | Food Returned |
|---------|--------|-----|---------------|--------------------|--------|--------|---------------|
| Mice | CD-1 | Male | 20-30 | 36 | CRL | No | NA |

Study Design

| Group No. | No. of Animals | Test Article | Vehicle | Route | Dose Volume (mL/kg) | Conc. (mg/mL) | Dose (mg/kg) |
|-----------|----------------|--------------|---------|-------|---------------------|---------------|--------------|
| 1 | 36 | S-(1) | 7% Ethanol: 3% Cremophor EL: 90% D5W | IV (Tail Vein) | 10 | 2 | 20 |

Sample Collection timing: Terminal blood (plasma) and brain specimens were collected at 9 times post-dose, with 4 mice per sample time. Sample collection times: 5, 15 min., 2, 8, 24, 32, 48, 72 and 96 hr post-dose (4 mice per sample time).

Blood collection: A terminal blood sample was collected from each mouse via cardiac puncture. The whole blood was collected on wet ice, spun down immediately (at 4° C.), and plasma stored frozen at −20° C. until analysis. The anticoagulant used was $K_2EDTA$. Brain Sample Collection: Whole brains were removed by dissection. Brains were collected on wet ice, weighed, and stored at −20° C.

TABLE 3

Mouse Plasma and Brain Levels of S-(1) after Single iv Dose

| Brain | Plasma |
|-------|--------|
| Cmax ng/ml 3726.6 | Cmax ng/ml 1550.2 |
| AUC(0-t) ng-hr/ml 64984.9 | AUC (0-t) ng-hr/ml 16870.2 |
| AUC (0-∞) ng-hr/ml 88742.9 | AUC (0-∞) ng-hr/ml 16951.2 |
| MRT (expo)hr 42.5 | MRT (expo)hr 17.6 |
| CL ml/hr 0.006 | CL ml/hr 0.024 |

Figure 2:
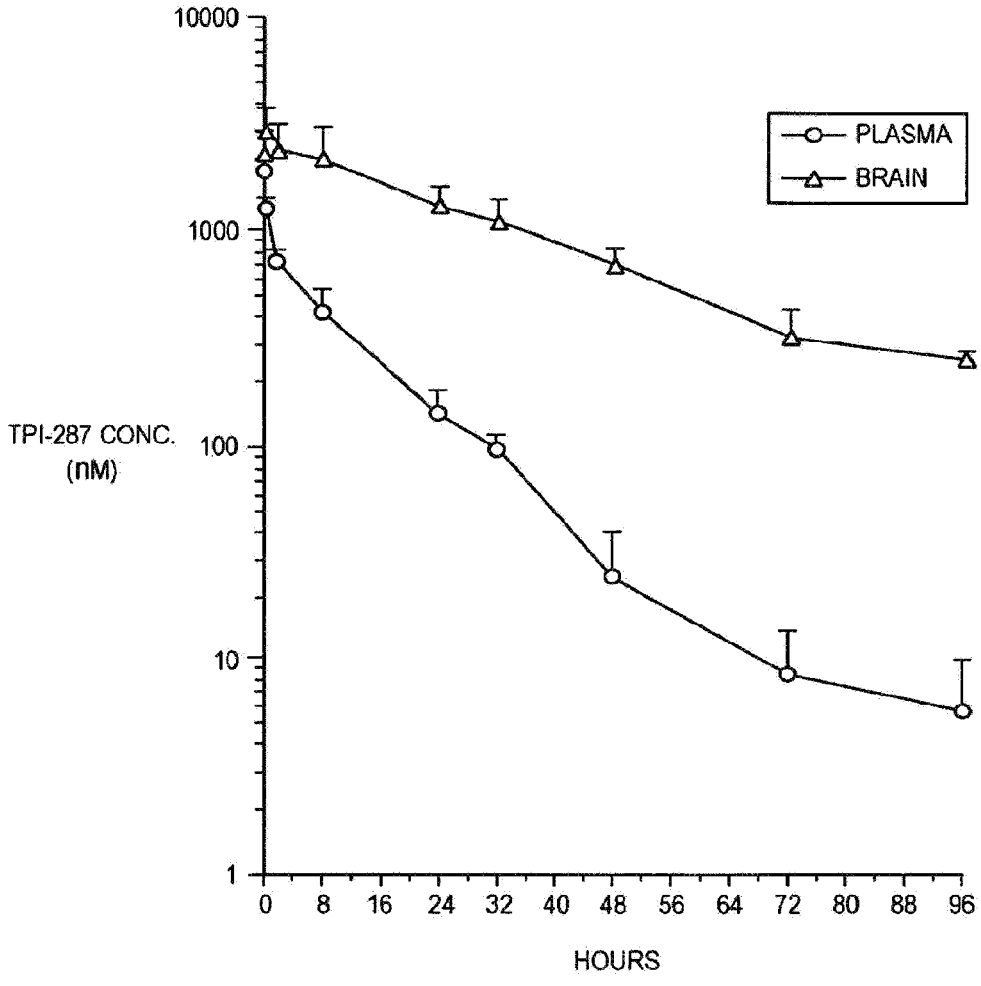
FIG. 2. Mouse Plasma and Brain Levels of S-(1) after single IV dose.

The results indicate that S-(1) is not impeded by the blood-brain barrier in the mouse model. See FIG. 2.

Antitumor Efficacy of S-(1) Against Human U251 CNS Tumor Cells Implanted in Mouse Brain:

Additional studies were conducted in animal models to determine the efficacy of S-(1) against brain tumors. In one study, the anti-tumor activity of S-(1) was evaluated both when administered alone and in combination with temozolomide, against intracerebrally (ic) implanted human U251 (glioblastoma) CNS tumor cells in male athymic nude mice.

Tumor Model: Each animal was implanted with one million U251 human CNS tumor cells from an in vitro cell line by ic injection with a 25 gauge needle. The day of tumor implantation (May 24, 2006) was designated as day 0. A sufficient number of mice were implanted so that animals with body weights in a range as narrow as possible were selected for the trial on the day of treatment initiation (day 1 after tumor implantation). Animals were randomly assigned to the treatment groups and individually identified by earmark codes.

Drug Formulation: On each day of treatment, the appropriate amount of S-(1) was formulated in 3% cremophor EL/7% ethanol/90% D5W at a concentration of 2 mg/mL. A portion of this solution was then diluted with the complete vehicle to achieve the lower dosing concentration of 1.2 mg/mL. Both concentrations of S-(1) were then kept at 37° C. and injected within 30 minutes of formulation on the basis of exact body weight using a volume of 0.1 mL/10 g of body weight. Temozolomide (Temodar, Schering Corporation) was prepared on each day of injection in Klucel+ tween 80 at a concentration of 4 mg/mL. Temozolomide was administered within 5 minutes of formulation on the basis of exact body weight using a volume of 0.2 mL/10 g of body weight.

Data Collection: Animal health surveillance was conducted and mortality data were collected daily. The animals were weighed twice weekly starting with the first day of treatment.

Study Duration: The study was terminated 100 days after tumor implantation. Any animal found moribund or whose body weight dropped below 14 g was euthanized prior to study termination.

Parameters Evaluated: Number of 100-day survivors, median day of death, and the increase in lifespan based on median day of death and expressed as a percentage (% ILS), median survival time and the % ILS based on median survival time.

Results:

The vehicle-treated control group had a median day of death and a median survival time of 10 days. All animals died or were euthanized due to moribundity between days 9 and 11. The maximum loss in mean body eight was 32% (7 g).

Due to the dehydrating effect of treatment with S-(1), animals in groups 2, 3, 5, and 6 that received treatment with S-(1) at a dosage of 20 or 12 mg/kg/dose were given 5% dextrose in lactated Ringer's solution to lessen the debilitating effects of the treatment. Administration of the Ringer's solution was initiated when animal body weights dropped by greater than 10% and continued until the animal recovered, died, or was euthanized.

Intravenous treatment with S-(1), administered at dosages of 20 and 12 mg/kg/dose on a q4d×3 schedule, resulted in a 60% and 45% ILS, respectively, whether the calculation was based on day of death or survival time. The corresponding median days of death and the median survival times were 16 and 14.5 days for the S-(1) dosages of 20 and 12 mg/kg/dose, respectively. One death occurred on day 2 in the group receiving treatment with the dosage of 20 mg/kg/dose. This death may have been treatment-related or may have been a delayed effect of the anesthesia used at the time of the ic tumor implant.

Treatment with temozolomide administered at a dosage of 80 mg/kg/dose given po q4d×3 was quite effective against the growth of the U251 CNS tumor cells with an ILS of 380% when calculated based on median day of death (48 days) and 400% when calculated based on median survival time (50 days). There was one survivor in this group at the time of study termination on day 100. Treatment with temozolomide was tolerated without treatment-related deaths and with only a minimal loss (8%, 2 g) in mean body weight.

Administration of S-(1) given iv at a dosage of 20 mg/kg/dose in combination with temozolomide given po at a dosage of 80 mg/kg/dose resulted in an ILS of 575%, with the median day of death and the median survival time both being 67.5 days. The maximum loss in mean body weight loss observed in this treatment group was 22% (5 g). The loss was recovered following cessation of treatment. One death occurred on day 5, two deaths occurred on day 9, and one death occurred on day 16, possibly from toxicity of S-(1). The remaining six animals in the group did respond to therapy with deaths occurring between days 64 and 90.

Figure 3:
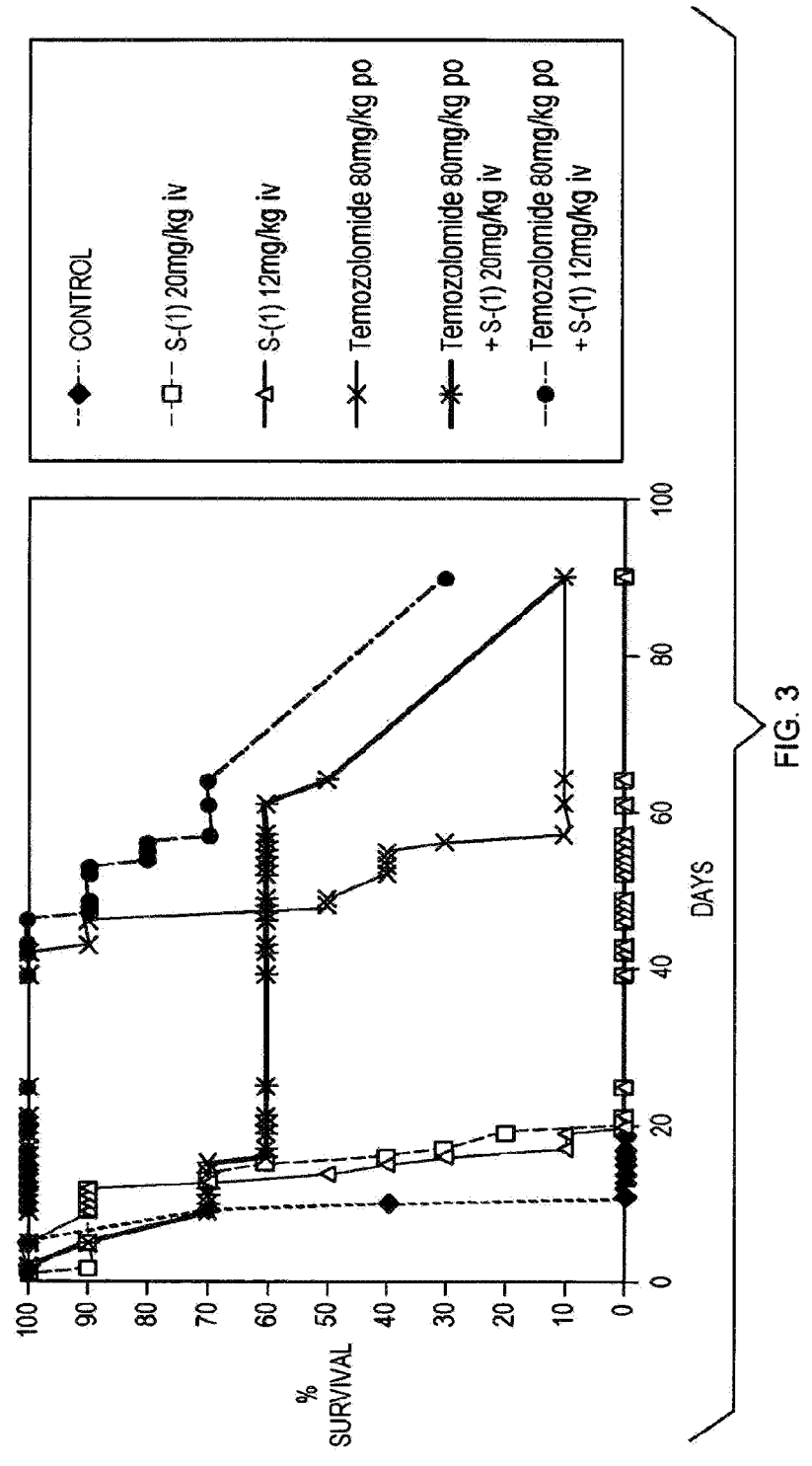
FIG. 3. Summary of U251 Orthotopic Intracranial Xenograft Study Data.
Figure 4A:
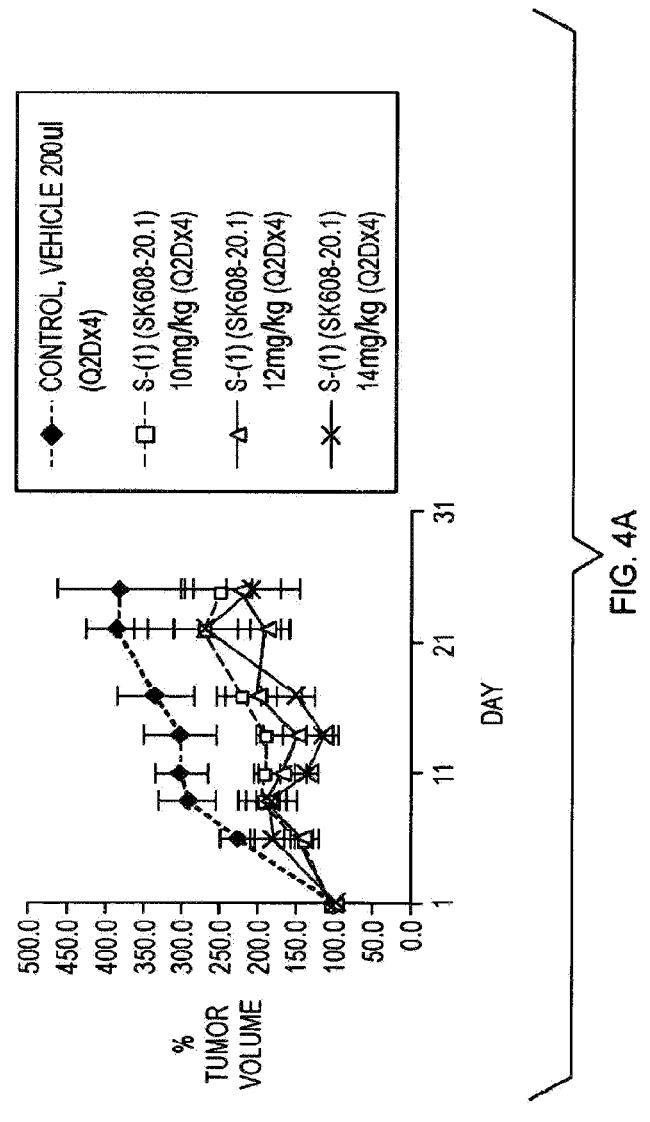
Figure 4B:
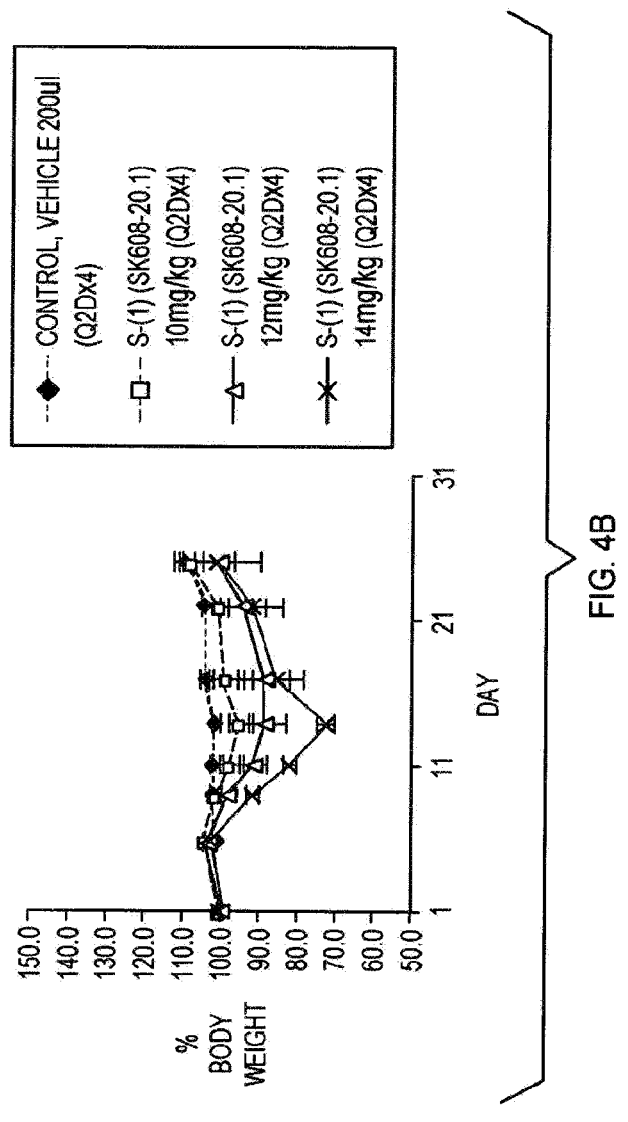
Figure 5B:
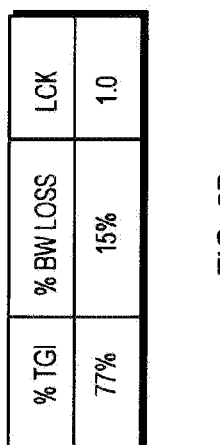
FIGS. 5A and 5B. Oral Efficacy of S-(1) in Neuroblastoma Xenograft.
Figure 5A:
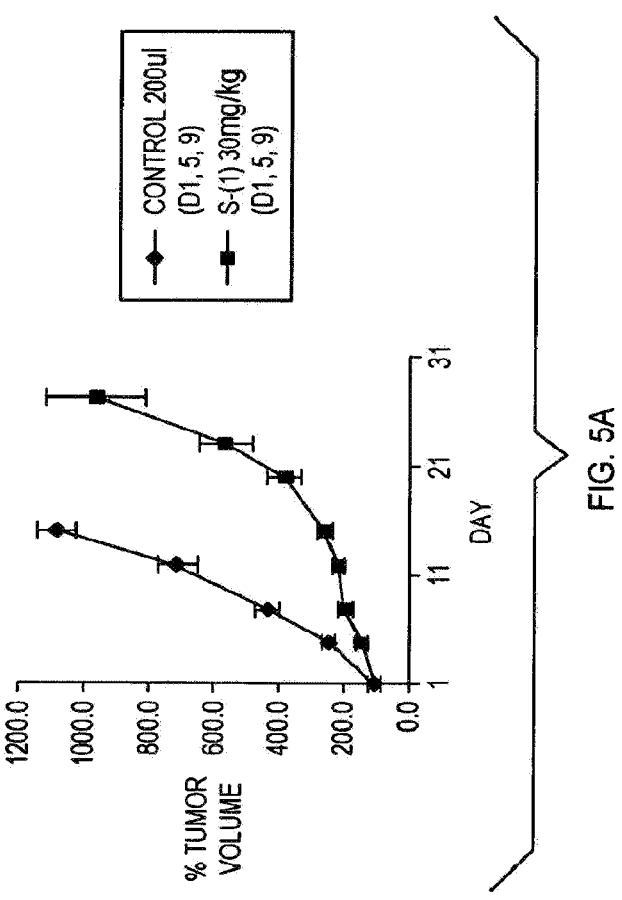
Figure 6B:
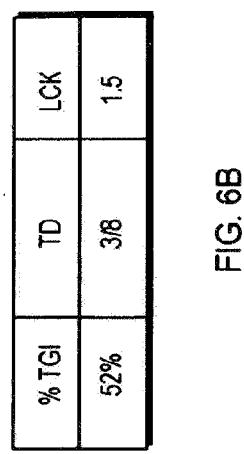
FIGS. 6A and 6B. S-(1) Oral Efficacy in Ovarian Tumor Xenograft.
Figure 6A:
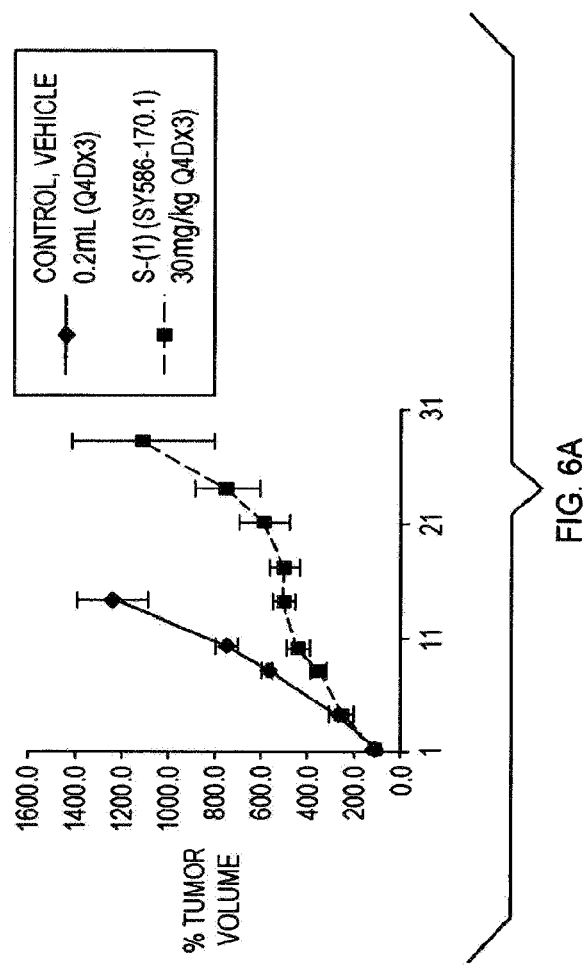
Figure 7B:
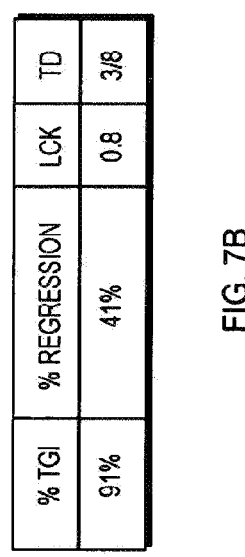
FIGS. 7A and 7B. S-(1) Oral efficacy in Glioblastoma Xenograft.
Figure 7A:
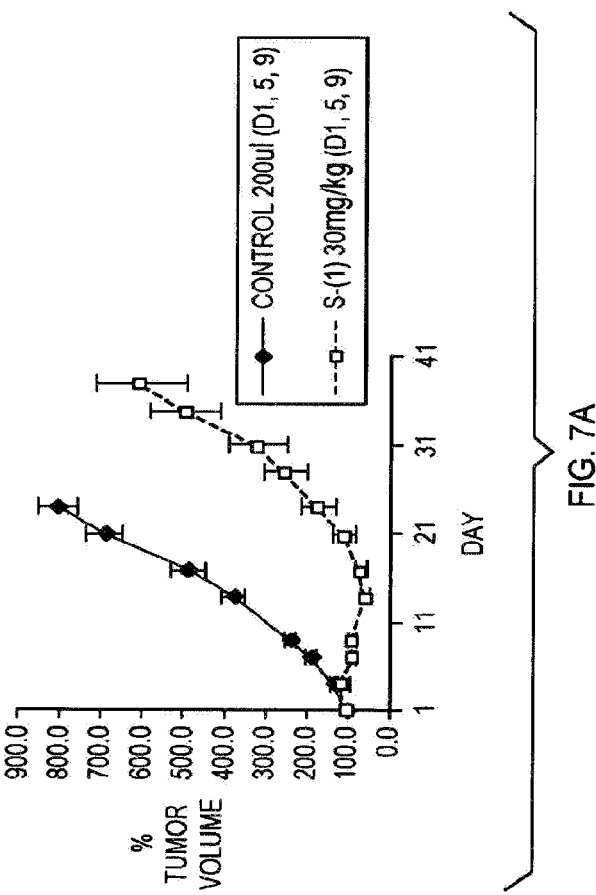
Figure 8B:
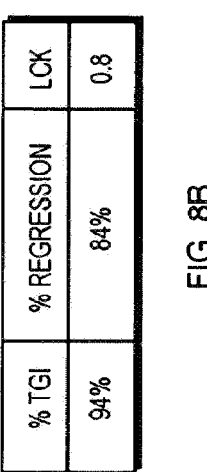
FIGS. 8A and 8B. IV efficacy of S-(1) in Glioblastoma Xenograft Model.
Figure 8A:
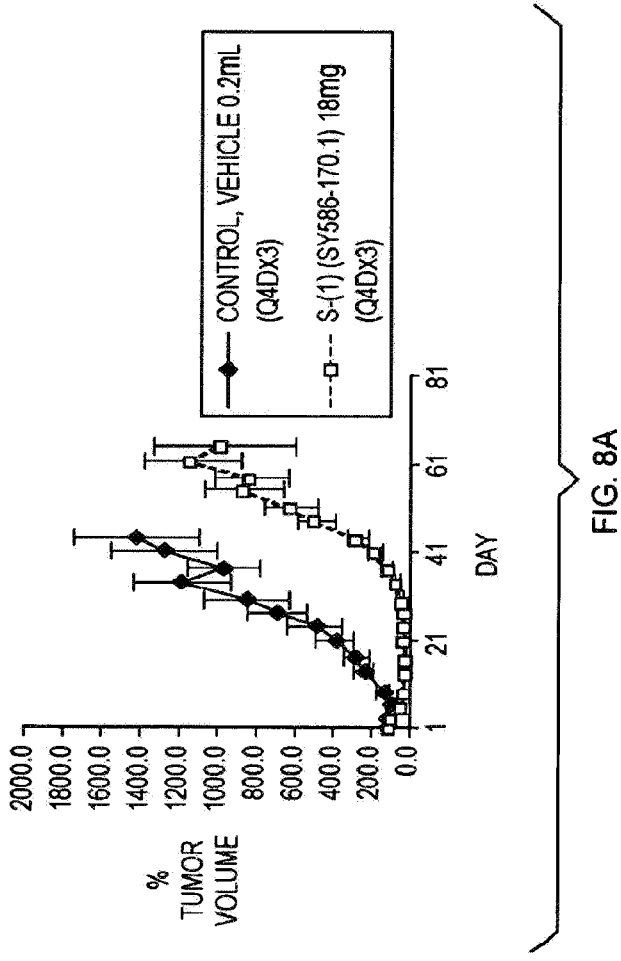
Figures 10A, 10B:
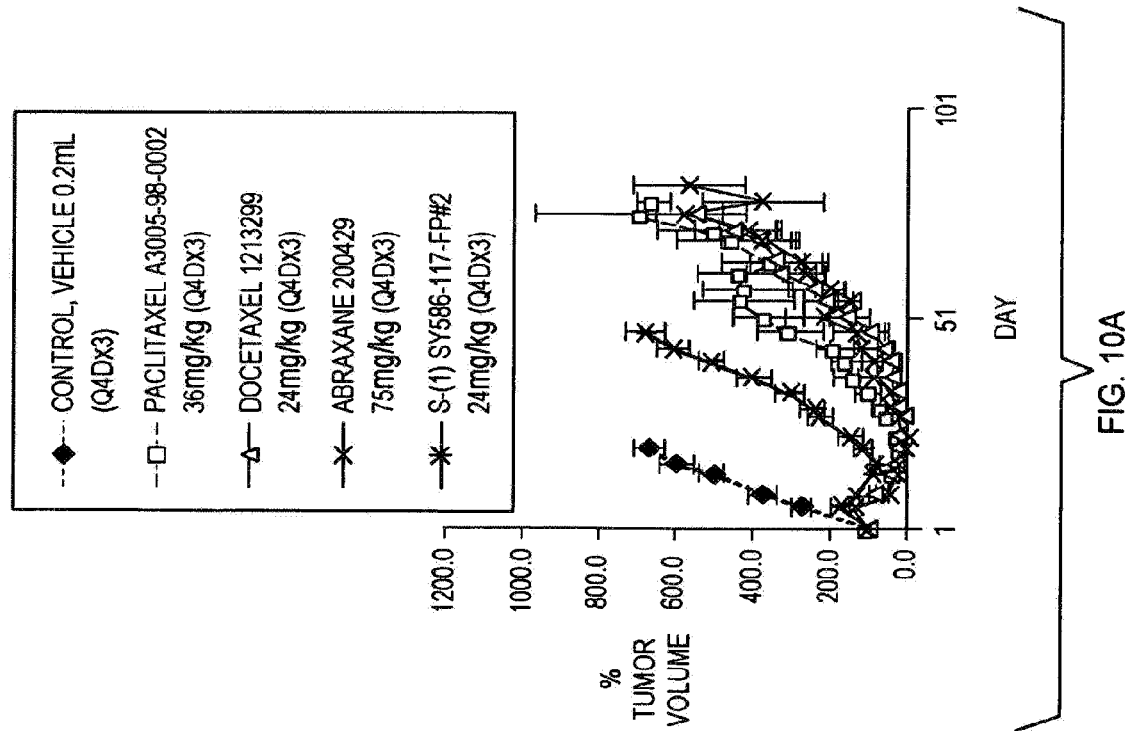
FIGS. 10A and 10B. Efficacy Comparison in Lung Tumor Xenograft Model
Figures 11A, 11B:
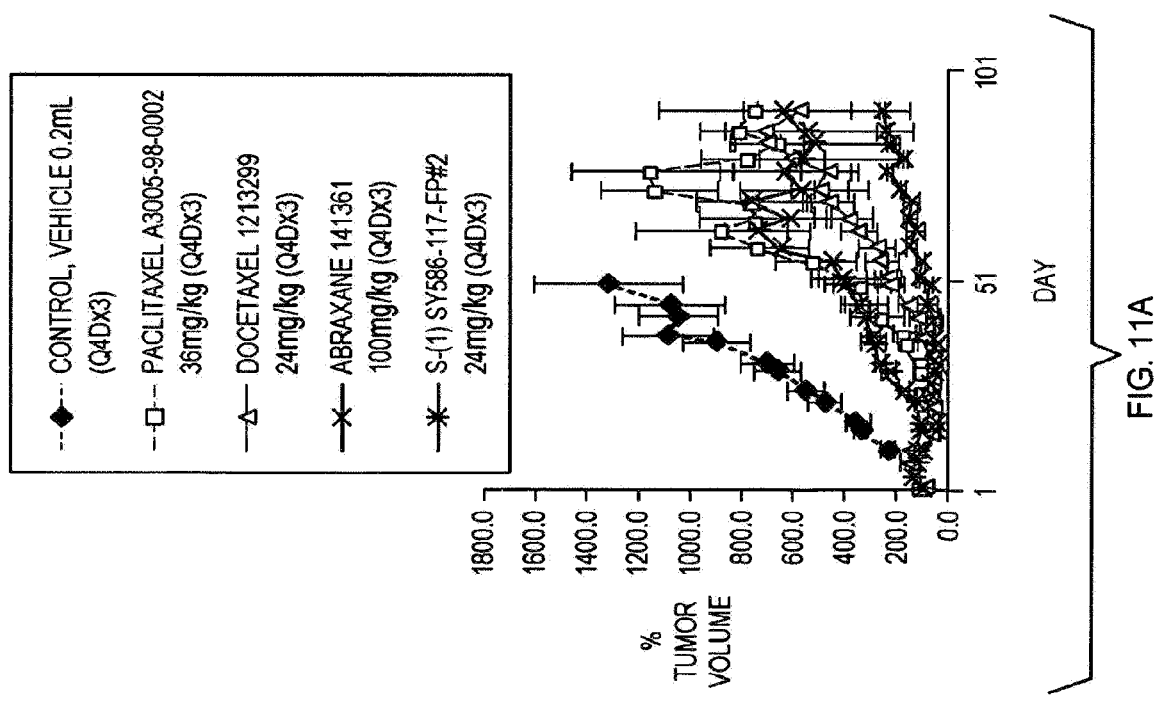
FIGS. 11A and 11B. Efficacy Comparison in Breast Tumor Xenograft Model
Figures 12A, 12B:
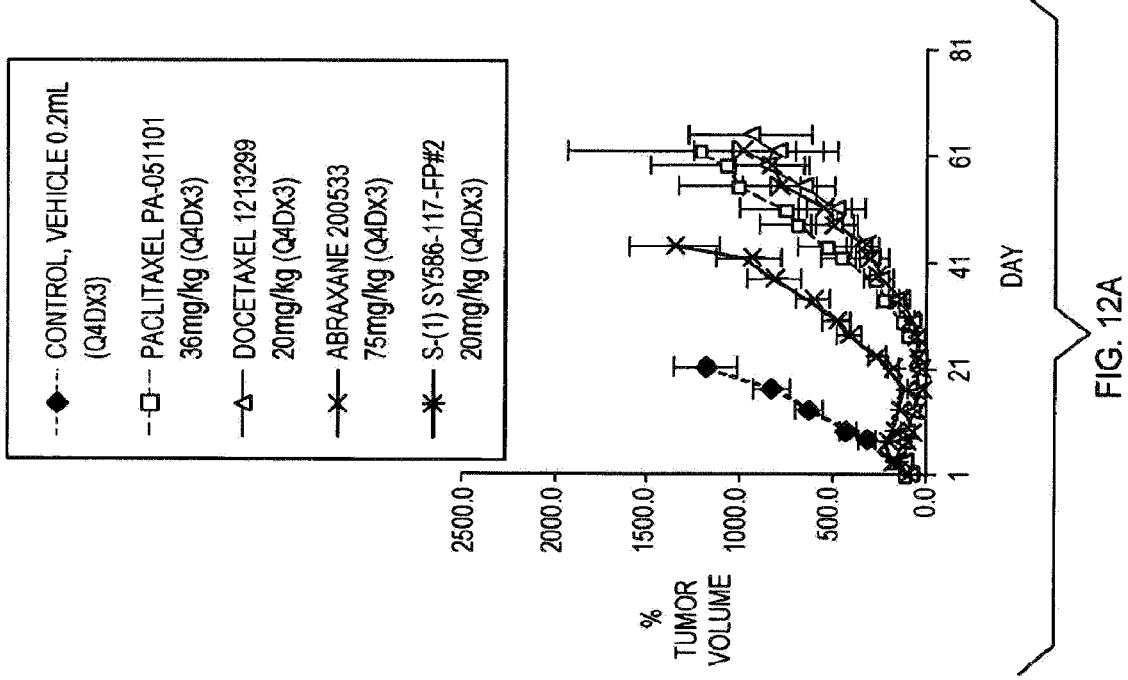
FIGS. 12A and 12B. Efficacy Comparison in HT 29 Colon Xenograft
Figure 13B:
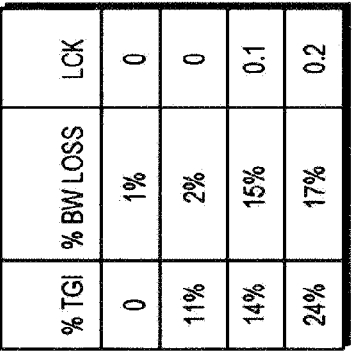
FIGS. 13A and 13B. Oral S-(1)+/−Avastin
Figure 13A:
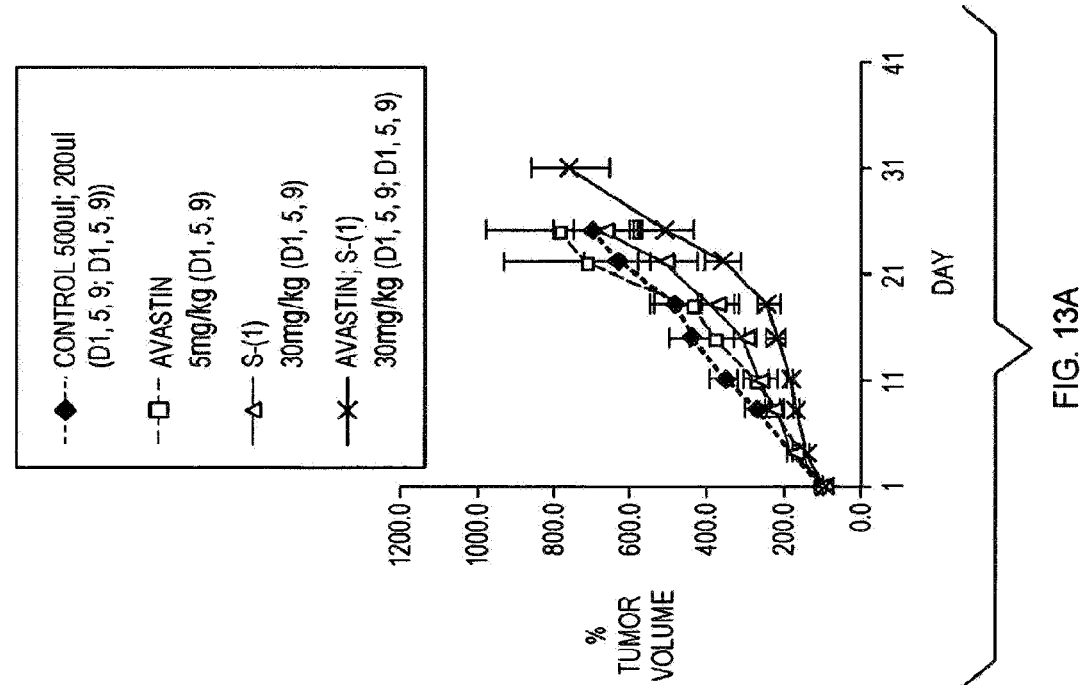
Figures 14A, 14B:
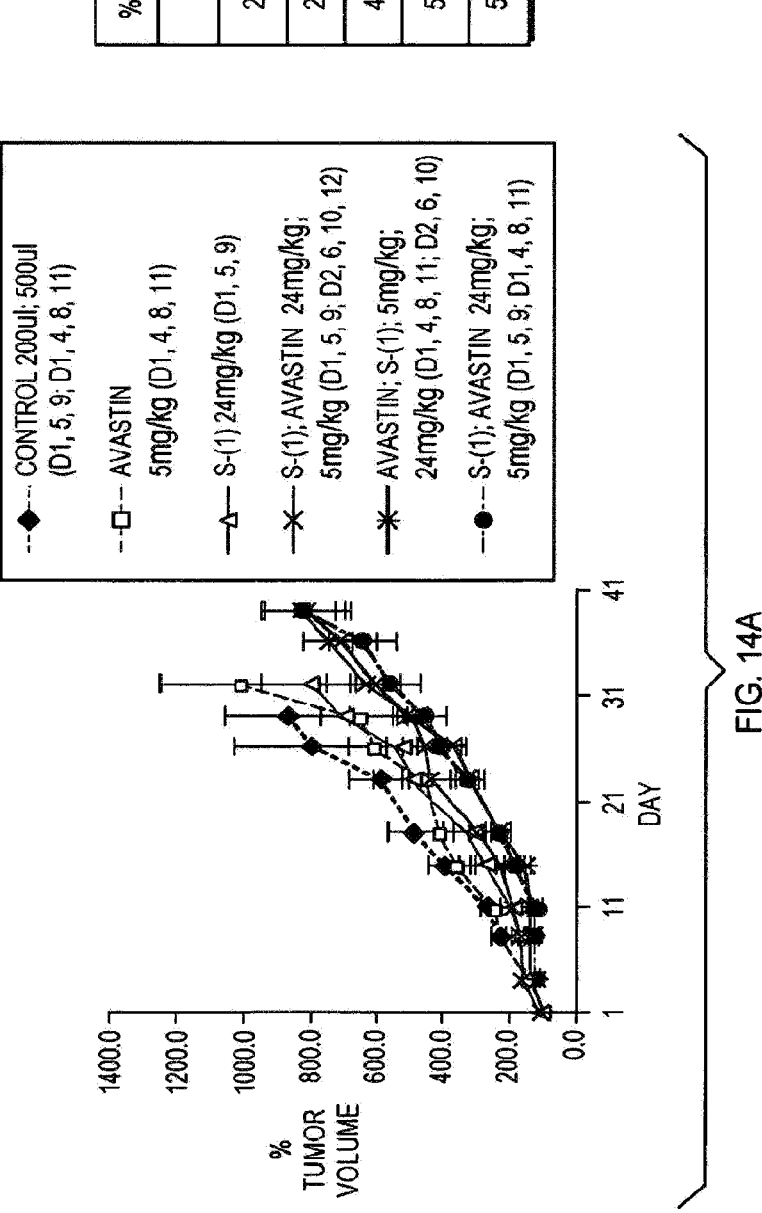
FIGS. 14A and 14B. Combination Efficacy of S-(1)+/−Avastin

The group receiving treatment with S-(1) at a dosage of 12 mg/kg/dose in combination with temozolomide at 80 mg/kg/dose responded more favorably than the group receiving the higher dosage of S-(1). The median day of death was day 73, with an ILS of 630%, and the median survival time was 75 days with an ILS of 650%. Results are shown in FIG. 3.

TABLE 4

| Summary of U251 Orthotopic Intracranial Xenograft Study | |
| --- | --- |
| S-(1) 20 mg/kg, ip.<br>QD1, 5, 9 Group 2 | 60% ILS (survivors day 100 = 0)<br>Group 2 vs. 2, P = 0.000 |
| S-(1) 12 mg/kg, ip.<br>QD1, 5, 9 Group 3 | 45% ILS (survivors day 100 = 0)<br>Group 1 vs. 3 P = 0.000 |
| TMZ 80 mg/kg, po.<br>QD1, 5, 9 Group 4 | 380% ILS (survivors day 100 = 1)<br>Group 2 vs 3, P = 0.450 |
| TMZ 80 mg/kg, po. +<br>S-(1) 20 mg/ip.<br>QD1, 5, 9 Group 5 | 575% ILS (survivors day 100 = 1)<br>Group 4 vs 5, P = 0.683 |
| TMZ 80 mg/kg, po. +<br>S-(1) 12 mg/kg ip.<br>QD1, 5, 9 Group 6 | 650% ILS (survivors day 100 = 3)<br>Group 4 vs. 6, P = 0.046<br>Group 5 vs. 6, P = 0.108 |

Monotherapy with temozolomide produced an excellent effect against the U251 human CNS tumor cells, while S-(1), administered alone, produced a moderate effect. Combination treatment with S-(1) and temozolomide was quite effective at both dosages of S-(1). The better response was seen in the combination group receiving the lower S-(1) dosage, possibly because of toxicity of S-(1) at the dosage of 20 mg/kg/dose.

Toxicology. Central Nervous System (CNS) Safety Study in Rats:

The objective of this study was to evaluate the acute pharmacological effects of S-(1) on the central nervous system following intravenous administration in the male albino rat. This study was conducted at ClinTrials BioResearch (CTBR, Montreal, Quebec, Canada) as a GLP study.

Results:

All animals were observed twice daily for signs of ill health or reaction to treatment, except on day of arrival and necropsy. A Functional Observation Battery (FOB) assessment, along with grip strength, hind limb splay and body temperature measurements were performed for all animals once pre-dose and at approximately 15 minutes, 1 hour, 4 hours, 8 hours and 24 hours post-dose. After the last observation, all animals were euthanized without further examination. There were no deaths or treatment-related clinical signs.

A single intravenous administration of S-(1) at 6.25, 12.5 or 25 mg/kg had no biological effect on central nervous system, when measured by qualitative assessment of the functional observational battery and quantitative assessment of grip strength, hind limb splay, and body temperature at approximately 15 minutes, 1, 4, 8 and 24 hours post-dose.

TABLE 5

| Results of CNS Safety Study | | | | |
| --- | --- | --- | --- | --- |
| Group/<br>Identification | Dose Level<br>(mg/kg) | Dose<br>Concentration<br>(mg/kg) | Dose Volume<br>(mL/kg) | No. of<br>Animals<br>Males |
| 1. Control | 0 | 0 | 3 | 8 |
| 2. S-(1) | 6.25 | 2.08 | 3 | 8 |
| 3. S-(1) | 12.5 | 4.17 | 3 | 8 |
| 4. S-(1) | 25 | 8.33 | 3 | 8 |

Conclusions: Dose levels of 6.25, 12.5 and 25 mg/kg had no biological effects on the central nervous system of male Sprague Dawley rats following administration by intravenous injection. The no adverse effect level for this study is 25 mg/kg.

Clinical Studies of S-(1)

Two Phase 1 trials examining the safety and pharmacokinetics of multiple ascending doses of single agent, intravenous S-(1), when administered in two different treatment schedules, are ongoing. Both trials have enrolled patients with advanced solid tumors, non-Hodgkin's lymphoma or Hodgkin's lymphoma that have recurred or progressed following at least standard therapy; patients with malignancies for which there is no standard therapy; patients who are not candidates for standard therapy; or patients who have chosen not to pursue standard therapy. In Study S-(1)-01, intravenous S-(1) is administered weekly for 3 consecutive weeks followed by one week of no therapy; treatment cycles are repeated every 28 days in patients who remain eligible for continued treatment. Study S-(1)-01 is currently being conducted in the United States. In Study S-(1)-02, intravenous S-(1) is administered every 3 weeks; treatment cycles are repeated every 21 days in patients who remain eligible for continued treatment. Study S-(1)-02 is currently being conducted in the United States and in Israel.

TABLE 6

| Clinical Studies of S-(1) | | |
| --- | --- | --- |
| Study No.<br>Phase | Patients Enrolled<br>Dose Group | Protocol Regimen |
| S-(1)-01<br>Phase 1 | 27<br>7 mg/m²: 4 pts<br>14 mg/m²: 4 pts<br>28 mg/m²: 4 pts<br>56 mg/m²: 4 pts<br>127.5 mg/m²: 7 pts<br>185 mg/m²: 4 pts | S-(1) i.v. in a 50% cremaphor,<br>50% ethanol formulation over 1<br>hour or less weekly x 3 followed<br>by 1 week of no therapy (28-day<br>treatment cycle) |
| S-(1)-02<br>Phase 1 | 20<br>56 mg/m²: 2 pts<br>84 mg/m²: 1 pt<br>126 mg/m²: 3 pts<br>185 mg/m²: 6 pts<br>160 mg/m²: 8 pts | S-(1) i.v. in a 15% cremphor,<br>85% ethanol formulation over<br>1 hour or less every 3 weeks<br>(21-day treatment cycle) |

Clinical Safety—Adverse Events:

Dose Limiting Toxicity: Dose limiting toxicity has been observed in one patient in Study S-(1)-01 who received 185 mg/m² of S-(1). The dose limiting toxicity was Grade 3 sensory neuropathy. Dose limiting toxicity has been observed in 2 patients in Study S-(1)-02 at a dose of 185 mg/m². In both patients, the dose limiting toxicity was Grade 3 sensory neuropathy.

Clinical Pharmacokinetics:

Pharmacokinetic data for the Phase 1 studies S-(1)-01 and S-(1)-02 are summarized in Table 7. Plasma pharmacokinetics of S-(1) were assessed following the first dose of S-(1) in both studies. Plasma samples were analyzed for S-(1) using a validated LC/MS-MS method. Two different formulations of S-(1) were administered in the two different Phase 1 studies: a 50:50 (w/v) formulation of Cremophor EL-P/ethanol, administered in the S-(1)-01 study, and a 15:85 (w/v) formulation of Cremophor EL-P/ethanol, administered in the S-(1)-02 study.

Analysis of the PK data revealed that the plasma AUC of S-(1) appeared to be relatively dose proportional, with a moderate level of interpatient variability. Plasma $t_{1/2}$ values ranged from 3.45-8.4 hours for the S-(1)-01 study, and from 3.43-8.96 for the S-(1)-02 study. Clearance did not appear to be dose-dependent in either study. There did not appear to be any difference in pharmacokinetic parameters, including $V_{ss}$, for the two different formulations of S-(1).

TABLE 7

| Dose (mg/m²) | AUC$_{0-24}$ (ng/ml*hr) | Cl (L/hr/m²) | Vss (L/m²) | $t_{1/2}$ (hr) |
|---|---|---|---|---|
| Plasma Pharmacokinetic Parameters for S-(1) | | | | |
| Study S-(1)-01 (50:50 Cremophor EL-P/ethanol formulation) | | | | |
| 14 | 457 ± 297 | 35.5 ± 29.7 | 23.2 ± 74.5 | 8.4 ± 11.5 |
| 28 | 682 ± 322 | 43.5 ± 14.5 | 309 ± 161 | 3.45 ± 1.09 |
| 56 | 2070 ± 888 | 28.6 ± 13.2 | 216 ± 70 | 5.66 ± 3.63 |
| 85 | 5970 ± 3900 | 16.6 ± 9.26 | 142 ± 75.6 | 5.52 ± 5.26 |
| 127.5 | 4460 ± 2140 | 30.2 ± 11.9 | 239 ± 116 | 6.59 ± 2.60 |
| Study S-(1)-02 (15:85 Cremophor EL-P/ethanol formulation) | | | | |
| 56 | 2530 ± 847 | 18.9 ± 9.53 | 232 ± 93.6 | 8.96 ± 7.09 |
| 84 | 3710 | 15.4 | 300 | — |
| 126 | 6110 ± 3030 | 22.1 ± 11.2 | 166 ± 105 | 6.27 ± 3.64 |
| 185 | 7260 ± 2620 | 24.7 ± 12.2 | 215 ± 116 | 3.43 ± 7.31 |

Summary of a Study of S-(1): Administered Weekly in Patients with Advanced Cancer:

In preclinical studies, S-(1) demonstrated antitumor activity against multiple human tumor xenografts in nude mice, including xenografts that expressed mdr-1 and that were resistant to other taxanes. The safety and tolerability of S-(1) when administered weekly for 60 minutes for 3 weeks followed by a 1 week rest (4 week cycle) was examined in this Phase 1 dose escalation study in patients (pts) with advanced neoplasms.

Treatment cohorts consisted of 3 pts and were expanded to 6 pts in the face of dose-limiting toxicity (DLT); pts could remain on study until the development of progressive disease or an intolerable adverse event. DLT was defined as Gr 4 heme toxicity lasting 7 days; febrile neutropenia, Gr 3 thrombocytopenia with bleeding, Gr 3 elevation of transaminases lasting 7 days or any other Gr 3/4 toxicity other than nausea or vomiting.

Results: 25 pts (M:F 16:9, median age 60, range 24-86) were enrolled in 7 dose levels ranging from 7-185 mg/m². Pts' cancers included colorectal (6 pts); NSCLC (2); prostate (2); squamous cell carcinoma (2) and 1 pt each with cervical, breast, ovarian, gastric, pancreatic, bladder endometrial, NSCLC, SCLC, glioblastoma, melanoma, renal cell and hepatocellular carcinoma. All pts but 1 had received prior chemotherapy (median no. prior treatments: 3 (range, 1-7). Drug related adverse events included nausea, vomiting, diarrhea, fatigue, anorexia, rash, anemia and peripheral neuropathy. DLT of Grade 3 peripheral neuropathy has been observed. PK data to date reveal that AUC is generally dose linear. At a dose of 127.5 mg/m², clearance was 30.2±11.9 L/hr/m² and $t_{1/2}$ 8.6±1.3 hrs. Anti-neoplastic activity was seen in a patient with pancreatic cancer.

In conclusion, S-(1) can be safely administered in doses of up to 185 mg/m² weekly×3 in heavily pre-treated patients. It is predicted that in chemo-naïve patients, or patients with more limited exposure to chemotherapy, that the dose could be escalated even further. S-(1) has activity in pancreatic cancer. PK is dose linear and predictable.

Summary of a Phase 1 Study of S-(1): Administered Every 21 Days in Patients with Advanced Cancer:

In preclinical studies, S-(1) suppressed the growth of multiple human tumor xenografts in nude mice, including xenografts that expressed mdr-1 and that were resistant to other taxanes. The safety and tolerability of S-(1) when administered every 21 days was examined in this Phase 1 dose escalation study in patients (pts) with advanced neoplasms.

S-(1) was administered over 1 hour every 21 days in ascending doses to groups of 3 pts. Treatment cohorts were expanded to 6 pts in the face of dose-limiting toxicity (DLT); pts could remain on study until the development of progressive disease or an intolerable adverse event. DLT was defined as Gr 4 heme toxicity lasting 7 days; febrile neutropenia, Gr 3 thrombocytopenia with bleeding, Gr 3 elevation of transaminases lasting 7 days or any other Gr 3/4 toxicity other than nausea or vomiting.

Results: 14 patients (M:F 5:9, median age 58.5, range 49-77) were enrolled in 5 dose levels ranging from 56-185 mg/m². Patients' cancers included colorectal (5 pts), esophageal (2), pancreatic (2), NSCLC (2), breast (2) and ovarian (1). All patients had received prior chemotherapy (median no. prior treatments: 3 (range, 2-10)). Drug related adverse events included mucositis, vomiting, diarrhea, neutropenia, thrombocytopenia, myalgias and peripheral neuropathy. Only 1 pt. experienced Gr 4 neutropenia. DLT of Gr 3 peripheral sensory neuropathy was observed at a dose of 185 mg/m². At a dose of 160 mg/m² no DLT was observed. 1 pt with pancreatic cancer had a confirmed response to S-(1). PK data reveal that AUC is generally dose linear. At a dose of 126 mg/m², clearance was 24.7±12.2 L/hr/m² and $t_{1/2}$ was 10.6±7.1 hrs.

It was determined that S-(1) can be safely administered in a dose of 160 mg/m² every 21 days in heavily pre-treated patients. It is predicted that in chemo-naïve patients, that the dose could be escalated even further. The dose limiting toxicity was Gr 3 peripheral neuropathy. S-(1) appears to have activity in pancreatic cancer. PK is dose linear and predictable.

Oral Dosing of the Compound of Formula S-(1):

The compound of formula S-(1) when dosed either oral or iv shows efficacy in mouse xenografts. From these efficacy studies and MTD studies, the "apparent oral bioavailability" of the compound of formula S-(1) in nude mice would be in the 40 to 80% range.

TABLE 8

| Formula S-(1) Injection Formulation Administered Orally: Mouse PK Parameters | | | |
|---|---|---|---|
| S-(1) - IV 10/mg/kg | | S-(1) - Oral 10 mg/kg | |
| $C_{max}$ (nM) | na | $C_{max}$ (nM) | 460 |
| $t_{max}$ (hr) | na | $t_{max}$ (hr) | 6.0 |
| t ½ (hr) | 6.1 | t ½ (hr) | 5.1 |
| AUC$_{last}$ (nM · hr) | 6298 | AUC$_{last}$ (nM · hr) | 3434 |
| AUC$_{inf}$ (nM · hr) | 7738 | AUC$_{inf}$ (nM · hr) | 3609 |
| CL (L/hr/kg) | 1.49 | F (%) | 47 |
| Vdss (L/kg) | 13.35 | | |

Efficacy of Orally Dosed S-(1) in Mouse Neuroblastoma Xenografts:

Summary of Experimental Protocol: Human neuroblastoma tumor cells were implanted via subcutaneous injection of $1\text{-}10\times10^6$ cells in nude mice. Tumors were allowed to grow to 200 mg+/−50 mg in size. Drug dosing was initiated, and tumor volume and body weight were recorded twice weekly.

Data Analysis:

The mean value for % body weight change and % tumor volume increase for each experimental group was plotted including error bars for the standard error of the mean. Other metrics for assessing antitumor effects include: % T/C values as calculated by the following formula:

$$\frac{\% \text{ Mean Tumor Volume of Treated Group}}{\% \text{ Mean Tumor Volume of Control Group}}$$

$$\text{Log Kill} = (T - C)/3.32 \times (Td)$$

T is the time in days for the median tumor volume to reach 1 gram in treated group C is the time in days for the median tumor volume to reach 1 gram in control group Td is the tumor doubling time in days Cures are excluded from T-C calculations Results are shown in FIGS. 4 to 9.

S-(1) Rat Oral Bioavailability:

IV formulation (Cremophor El P/alcohol) and a suspension of the compound of formula S-(1) in aqueous medium.

Several studies were performed to investigate specific parameters. It was found that there is a gender difference but it does not influence bioavailability (F) overall, the formulation dilution does not impact F, there is saturation of the absorption that seems formulation dependent, and the data is reproducible between experiments.

From the solubility and compatibility studies between the compound of formula S-(1) and excipients that could be used, a reasonable list of formulations were evaluated in vivo. Pharmacokinetics results for 9 formulations administered to female rats by oral gavage are listed in Table 9 below.

TABLE 9

| AUC of Selected Evaluated Oral Formulations | | |
|---|---|---|
| | AUC last (hr*ng/ml) | AUCinf/Dose (hr*kg*ng/mL/mg) |
| Cremophor:EtOH 50:50/dil. 1:9 | 2220 | 426 |
| Tween 80:EtOH:Labrafil:Labrasol 25:25:35:35/dil. 1:1 | 5740 | 427 |
| Solutol:EtOH 60:40/dil. 1:1 | 6590 | 503 |
| Vit E-TPGS:Cre:EtOH:D5W 50:17:17:16/dil. 1:3 | 1450 | 266 |
| Solutol:Cre:EtOH:D5W 50:17:17:16/dil. 1:3 | 2370 | 431 |
| Lutrol:Cre:EtOH:D5W 40:20:20:20/dil. 1:3 | 2380 | 436 |
| Oleic Acid:Cre:Captex:Capmul:D5W 8:25:33:17:17/dil. 1:3 | 2610 | 555 |
| Solutol:EtOH:Labrafil:labrasol 50:10:25:15/dil. 1:1 | 2850 | 475 |
| Gelucire:Labrafil:PEG300 60:20:20/dil. 1:1 | 3120 | 520 |

In addition, when contemplating oral administration, one typically tries to evaluate the oral bioavailability of the compound. Using the 50:50 Cremophor:Ethanol formulation as a case study given orally (AUC last: 2540; norm AUCinf: 477), F was calculated using two different IV formulations as reference, the 50:50 Cremophor:Ethanol and the 15:85 Cremophor:Ethanol As shown in Table 10 below, the calculated F value is significantly impacted by the PK values of the IV reference.

TABLE 10

| Calculated F | | | |
|---|---|---|---|
| | AUC last (hr*ng/ml) | AUCinf/Dose (hr*kg*ng/mL/mg) | Calculated F (%) |
| Cremophor:EtOH 50:50/ dil. 1:9 dosed IV | 14600 | 2040 | ~23% |
| Cremophor:EtoH 15:85/ dil. 1:9 dosed IV | 4470 | 970 | ~49% |

Accordingly, the invention comprises a polyethoxylated castor oil formulation comprising the compound of formula S-(1). Preferably, the polyethoxylated castor oil formulation comprises about 50% ethanol and about 50% polyethoxylated castor oil or about 85% ethanol and about 15% polyethoxylated castor oil.

The invention claimed is:

1. A method for the treatment of cancer in a patient in need thereof, comprising orally administering to the patient a compound of Formula S-(1):

S-(1)

wherein:

the cancer is astrocytoma, craniopharyngioma, glioma, ependymoma, neuroglioma, oligodendroglioma, glioblastoma multiforme, meningioma, medulloblastoma, or a primitive neuroectoderm; and the compound of Formula S-(1) is administered at a unit dose of about 15 mg to about 250 mg.

2. The method of claim 1, wherein the unit dose comprises about 15 mg, about 50 mg, about 80 mg, about 100 mg, about 150 mg, about 200 mg, or about 250 mg of the compound of Formula S-(1).

3. The method of claim 1, further comprising administering to the patient an additional therapy selected from radiotherapy, surgical removal of a tumor, hormonal agents, antibodies, antiangiogenics, COX-2 inhibitors, taxanes, temozolomide, cisplatin, 5-fluorouracil, taxotere, gemcitabine, topoisomerase II inhibitor, topoisomerase I inhibitor, tubulin interacting agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy, and aromatase.

4. The method of claim 1, wherein the compound of Formula S-(1) is administered:

once every 7 days, in a 7 day cycle for at least one cycle;

once every 14 days, in a 14 day cycle for at least one cycle;

once every 21 days, in a 21 day cycle for at least one cycle; or once every 7 days for three weeks, followed by a 7 day rest period, in a 28 days cycle, for at least one cycle.

5. The method of claim 1, wherein the compound of Formula S-(1) is administered in a composition further comprising a pharmaceutically acceptable carrier.

6. A method for the treatment of cancer in a patient in need thereof, comprising parenterally administering to the patient a compound of Formula S-(1):

S-(1)

wherein:

the cancer is astrocytoma, craniopharyngioma, glioma, ependymoma, neuroglioma, oligodendroglioma, glioblastoma multiforme, meningioma, medulloblastoma, or a primitive neuroectoderm; and the compound of Formula S-(1) is administered at a unit dose of about 200 mg to about 400 mg.

7. The method of claim 6, wherein the unit dose comprises about 200 mg, about 250 mg, about 300 mg, about 350 mg, or about 400 mg of the compound of Formula S-(1).

8. The method of claim 6, the parenteral administration is an intravenous injection or an intravenous infusion.

9. The method of claim 6, further comprising administering to the patient an additional therapy selected from radiotherapy, surgical removal of a tumor, hormonal agents, antibodies, antiangiogenics, COX-2 inhibitors, taxanes, temozolomide, cisplatin, 5-fluorouracil, taxotere, gemcitabine, topoisomerase II inhibitor, topoisomerase I inhibitor, tubulin interacting agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy, and aromatase.

10. The method of claim 6, wherein the compound of Formula S-(1) is administered:

once every 7 days, in a 7 day cycle for at least one cycle;

once every 14 days, in a 14 day cycle for at least one cycle;

once every 21 days, in a 21 day cycle for at least one cycle; or once every 7 days for three weeks, followed by a 7 day rest period, in a 28 days cycle, for at least one cycle.

11. The method of claim 6, wherein the compound of Formula S-(1) is administered in a composition further comprising a pharmaceutically acceptable carrier.

12. A method for the treatment of cancer in a patient in need thereof, comprising administering to the patient a therapeutically effective amount of a compound of Formula S-(1):

S-(1)

wherein:

the cancer is astrocytoma, craniopharyngioma, glioma, ependymoma, neuroglioma, oligodendroglioma, glioblastoma multiforme, meningioma, medulloblastoma, or a primitive neuroectoderm; and the administration results in an in vivo plasma profile for the compound of Formula S-(1) comprising a mean area under the curve from dosing time to twenty four hours ($AUC_{0-24}$) of about 457 to 7,260 h*ng/mL.

13. The method of claim 12, wherein the compound of Formula S-(1) is administered:

orally at a unit dose of about 15 mg to about 250 mg; or parenterally at a unit dose of about 200 mg to about 400 mg.

14. The method of claim 13, wherein the compound of Formula S-(1) is administered:

orally at a unit dose of about 15 mg, about 50 mg, about 80 mg, about 100 mg, about 150 mg, about 200 mg, or about 250 mg of the compound of Formula S-(1); or parenterally at a unit dose of about 200 mg, about 250 mg, about 300 mg, about 350 mg, or about 400 mg of the compound of Formula S-(1).

15. The method of claim 13, wherein the parenteral administration is an intravenous injection or an intravenous infusion.

16. The method of claim 12, further comprising administering to the patient an additional therapy selected from radiotherapy, surgical removal of a tumor, hormonal agents, antibodies, antiangiogenics, COX-2 inhibitors, taxanes, temozolomide, cisplatin, 5-fluorouracil, taxotere, gemcitabine, topoisomerase II inhibitor, topoisomerase I inhibitor, tubulin interacting agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy, and aromatase.

17. The method of claim 12, wherein the compound of Formula S-(1) is administered:

once every 7 days, in a 7 day cycle for at least one cycle;

once every 14 days, in a 14 day cycle for at least one cycle;

once every 21 days, in a 21 day cycle for at least one cycle; or once every 7 days for three weeks, followed by a 7 day rest period, in a 28 days cycle, for at least one cycle.

18. The method of claim 12, wherein the compound of Formula S-(1) is administered in a composition further comprising a pharmaceutically acceptable carrier.

* * * * *